United States Patent [19]
Åkerblom et al.

[11] Patent Number: 6,124,354
[45] Date of Patent: Sep. 26, 2000

[54] ARYLCYCLOALKANE CARBOXYLIC ESTERS, THEIR USE, PHARMACEUTICAL COMPOSITIONS AND PREPARATION

[75] Inventors: Eva Åkerblom, Uppsala; Martin Haraldsson, Täby; Rolf Johansson, Huddinge; Katarina Beierlein, Uppsala; Birger Sjöberg, Sollentuna; Erik Ringberg, Uppsala; Birgitta Weinz, Sollentuna, all of Sweden

[73] Assignee: Pharmacia & Upjohn AB, Stockholm, Sweden

[21] Appl. No.: 09/230,164

[22] PCT Filed: Jul. 23, 1997

[86] PCT No.: PCT/SE97/01310

§ 371 Date: Apr. 12, 1999

§ 102(e) Date: Apr. 12, 1999

[87] PCT Pub. No.: WO98/04517

PCT Pub. Date: Feb. 5, 1998

[30] Foreign Application Priority Data

| Jul. 29, 1996 | [SE] | Sweden | 9602887 |
| Jul. 29, 1996 | [SE] | Sweden | 9602888 |
| Jul. 29, 1996 | [SE] | Sweden | 9602889 |
| Jul. 29, 1996 | [SE] | Sweden | 9602890 |

[51] Int. Cl.$^7$ .......................... A61K 31/216; A61P 1/00; A61P 13/10
[52] U.S. Cl. .......................... 514/530; 514/438; 514/531; 514/534; 549/77; 560/102
[58] Field of Search .................. 560/102; 514/530, 514/531, 534, 438; 549/77

[56] References Cited

U.S. PATENT DOCUMENTS

| 4,418,202 | 11/1983 | Fayter, Jr. | 549/496 |
| 5,064,850 | 11/1991 | Audia | 514/406 |
| 5,086,054 | 2/1992 | Parish | 514/239 |
| 5,817,679 | 10/1998 | Shen | 514/339 |

FOREIGN PATENT DOCUMENTS

| 20382687 | 8/1990 | European Pat. Off. . |
| 72168881 | 9/1973 | France . |
| 7289411 | 5/1991 | Germany . |

OTHER PUBLICATIONS

Bannard RAB et al. Can. J. Physiol. Pharmacol. 47(2), 1036–8, 1969.
Coleman I W et al. Can. J. Physiol. Pharmacol. 44, 745–64, 1966.
Su TP et al. J. Pharmacol. Exp. Ther. 259(2), 543–50, 1991.
Tilford CH et al. J. Amer. Chem. Soc. 69, 2902–2906, 1947.
J. H. Parkkari et al., Canadian Journal of Chem., vol. 43, 3119–3128, (1965).
R. W. Brimblecombe et al., Br. J. Pharmac. vol. 39, 822–830, (1970).
A. A. Casselman et al., J. Chromatog., vol. 52, 138–140 (1970).
F. C. Tortella et al., European Journal of Pharm., vol. 155, 69–75, (1988).
R. L. Hudkins et al., Med. Chem., vol. 34, 2984–2989, (1991).
R. L. Hudkins et al., Med. Chem. Res., vol. 2, 173–180, (1992).
S. N. Calderon et al., J. Med. Chem., vol. 37, 2285–2291, (1994).
Robert L. Hudkins et al, European Journal of Pharmacology, vol. 231, 1993, pp. 485–488.
James F. Stubbins et al, Med Chem Res, vol. 2, 1992, pp. 384–393.
R.A.B. Bannard et al, Canadian Journal of Chemistry, vol. 40, 1962, pp. 1909–1916.

*Primary Examiner*—Evelyn Mei Huang
*Attorney, Agent, or Firm*—Birch, Stewart, Kolasch & Birch, LLP

[57] ABSTRACT

This invention relates to the use of 2-(diisopropylamino)-ethyl-1-phenyl-cyclopentane-carboxylate or 2-(diisopropylamino)-ethyl-1-phenyl-cyclohexane-carboxylate, or a pharmaceutically accceptable salt thereof, for treatment of urinary incontinence or irritable bowel syndrome (IBS).

3 Claims, No Drawings

ARYLCYCLOALKANE CARBOXYLIC ESTERS, THEIR USE, PHARMACEUTICAL COMPOSITIONS AND PREPARATION

This application is the national phase under 35 U.S.C. §371 of prior PCT International Application No. PCT/SE97/01310 which has an International filing date of Jul. 23, 1997 which designated the United States of America.

FIELD OF THE INVENTION

The present invention relates to arylcycloalkane carboxylic esters having pharmacological properties, and to processes for their preparation. The invention also relates to pharmaceutical compositions containing arylcycloalkane carboxylic esters, methods of treating disorders related to urinary incontinence and irritable bowel syndrome (IBS), respectively, by administering an arylcycloalkane carboxylic ester, as well as methods for the manufacture of pharmaceutical compositions for treating disorders related to urinary incontinence and irritable bowel syndrome (IBS), respectively.

BACKGROUND OF THE INVENTION

A number of arylcycloalkane carboxylic esters, including arylcyclopropane, arylcyclobutane, arylcyclopentane and arylcyclohexane carboxylic acid esters, are known to possess anticholinergic activity. Some of them have a pronounced spasmolytic or anticonvulsant activity and have therefore been proposed to be used as substitutes for atropine in the treatment of sarin poisoning (sarin is an organophosphorous anticholinesterase agent acting as a nerve gas). Other activities related to that type of compounds are antipsychotic, anti-ischemic, anti-stroke and antidementia.

Specific arylcyclopropane carboxylic esters having anticholinergic activities are, for example, described in Beres, J. A., et al., J. Pa. Acad. Sci. (1992), 66(1), 2; U.S. Pat. No. 4,418,202; Mnjoyan, A. L., et al., Arm. Khim. Zh. (1976), 29(2) 194–9; Kuzuna, S., et al., Takeda Kenyosho Hu (1975), 34(4), 467–73; and WO 92/02481.

Arylcyclobutane carboxylic esters having anticholinergic activities are, for example, described in Bannard, R. A. B., et al., Can. J. Phys. Pharm. 47 (1969) 1036 (2',2'-diisopropylaminoethyl 1-phenylcyclobutane-carboxylate, 1'-methylpiperidyl-4' 1-phenylcyclobutane-carboxylate); CH—B—240160 (diethylaminoethyl 1-phenylcyclobutanecarboxylate); Parkkari, J. H., et al., Can. J. Chem. 43 (1965) 3119 (N-methyl-4-piperidyl 1-p-methylphenylcyclobutanecarboxylate, N-methyl-4-piperidyl 1-p-methoxyphenylcyclobutanecarboxylate); and Mnoyan, A.L. et al., supra (dimethylaminoethyl and diethylaminoethyl 1-benzophenylcyclobutylcarboxylates).

Arylcyclopentane carboxylic esters having anticholinergic activities are, for example, described in Bannard, R. A. B., et al., Can. J. Chem. 40 (1962) 1909–1916; Stubbins, J. F., et al, Med. Chem. Res. 2 (1992) 384–393; JP-A-02062823; U.S. Pat. No. 3,317,526; FR-A-1461314; FR-A-2155927; DD-A-289411 and FR-A-2168881.

Arylcyclohexane carboxylic esters having anticholinergic activities are, for example, described in Zbigniew, J., et al., Pol. J. Pharmacol. Pharm. 35 (1983) 103–107; Tsung-Ping Su et al., Pharmacology and Exp. Therapeutics 259 (1991) 543–550; Wolinski, J., and Cessak, M., Acta Pol. Pharm. 36 (1979) 635–40; WO 92/02481 and FR-A-2155927.

SUMMARY OF THE INVENTION

According to the present invention it has now been found that a defined group of arylcyclopropane, arylcyclobutane, arylcyclopentane and arylcyclohexane carboxylic esters, some of which are novel compounds, possess a selective antimuscarinic activity on the urinary bladder smooth muscle, and on the small intestine muscle, and are therefore indicated for the treatment of disorders of the urinary bladder, such as urge incontinence, as well as for the treatment of disorders of the small intestine, such as irritable bowel syndrome (IBS).

In one aspect, the present invention provides novel arylcycloalkane carboxylic esters of the general Formula I:

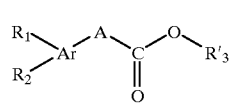

wherein:

A is an optionally substituted cycloalkane ring having 3 to 6 carbon atoms and attached at a single ring carbon atom thereof, Ar is phenyl or heteroaryl having 5 or 6 ring members, $R_1$ and $R_2$ independently are hydrogen, lower alkyl, lower alkoxy, halo, hydroxy, trifluoromethyl, nitro or amino, or $R_1$ and $R_2$ together form lower alkylenedioxy or optionally substituted benzo, and $R'_3$ is (i) —$(CH_2)_n NR_{10},R_{11}$, in which n is 2 or 3 and $R_{10}$ and $R_{11}$ each are lower alkyl or $R_{10}$ and $R_{11}$ together with the nitrogen atom form a saturated azacyclic or azabicyclic ring system; or (ii) —$(CH_2)_m$-Q, in which m is 0 or 1 and Q is the residue of a saturated azacyclic or azabicyclic ring system coupled via a carbon atom thereof, with the provisos that (i) when A is a cyclopropane ring which is unsubstituted or mono-substituted by lower alkyl or lower alkenyl, Ar is phenyl, $R'_3$ is —$(CH_2)_n NR_{10},R_{11}$, and $R_{10}$ and $R_{11}$ are lower alkyl, then $R_{10}$ and $R_{11}$ contain together at least six carbon atoms;

(ii) when A is a cyclopropane ring, Ar is phenyl, $R'_3$ is —$(CH_2)_n NR_{10},R_{11}$, n is 2, and $R_{10}$ and $R_{11}$ together with the nitrogen atom form a pyrrolidine ring, or $R'_3$ is —$(CH_2)_m$-Q, m is 0, and Q is a tropanyl ring, then the cyclopropane ring is at least mono-substituted;

(iii) when A is an unsubstituted cyclobutane ring, Ar is phenyl, and $R_1$ and $R_2$ are hydrogen, then $R'_3$ is other than diisopropylaminoethyl, diethylaminoethyl and N-methyl-4-piperidyl;

(iv) when A is an unsubstituted cyclobutane ring, Ar is phenyl, $R_1$ is hydrogen, and $R_2$ is p-methyl or p-methoxy, then $R'_3$ is other than N-methyl-4-piperidyl;

(v) when A is an unsubstituted cyclobutane ring, Ar is phenyl and $R_1$ and $R_2$ together form benzo, then $R'_3$ is other than dimethylaminoethyl and diethylaminoethyl;

(vi) when A is a cyclopentane ring, and Ar is phenyl, then the cyclopentane ring is at least mono-substituted;

(vii) when A is an unsubstituted cyclohexane ring, Ar is phenyl, $R'_3$ is —$(CH_2)_n NR_{10} R_{11}$, and $R_{10}$ and $R_{11}$ are lower alkyl, then $R_{10}$ and $R_{11}$ contain together at least six carbon atoms; and (viii) when A is a cyclohexane ring, Ar is phenyl, $R'_3$ is —$(CH_2)_m$-Q, and m is 0, then the cyclohexane ring is at least mono-substituted; or a pharmacologically acceptable salt thereof.

The cycloalkane ring A may be substituted at one or more ring carbons (mono- or di-substituted at each carbon), preferably with a substituent or substituents independently selected from lower alkyl, lower alkoxy, lower alkoxy-lower alkyl, cycloalkyl, lower alkenyl, lower hydroxyalkyl, benzyloxy-lower alkyl, trifluoromethyl, hydroxy, oxo or spiro-coupled lower alkylene or lower alkylenedioxy.

Preferably, A is a group of the general Formula II, III, IV or V:

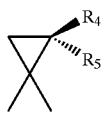

II

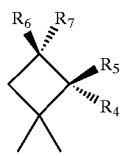

III

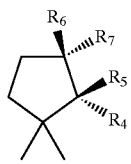

IV

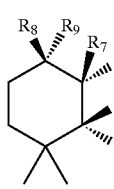

V wherein:
$R_4$, $R_5$, $R_6$, $R_7$, $R_8$ and $R_9$ independently are hydrogen, lower alkyl, lower alkoxy, lower alkoxy-lower alkyl, cycloalkyl, lower alkenyl, lower hydroxyalkyl, benzyloxy-lower alkyl, trifluoromethyl or hydroxy, or either $R_4$ and $R_5$ or $R_6$ and $R_7$ or $R_8$ and $R_9$ together form lower alkylene, lower alkylenedioxy or oxo.

Provisos (i) to (viii) given above for Formula I, are then defined as:

(i) when A is a group of Formula II, Ar is phenyl, $R'_3$ is —$(CH_2)_n NR_{10}R_{11}$, $R_{10}$ and $R_{11}$ are lower alkyl, and one of $R_4$ and $R_5$ is hydrogen and the other is hydrogen, lower alkyl or lower alkenyl, then $R_{10}$ and $R_{11}$ contain together at least six carbon atoms;

(ii) when A is a group of Formula II, Ar is phenyl, $R'_3$ is —$(CH_2)_n NR_{10}R_{11}$, n is 2, and $R_{10}$ and $R_{11}$ together with the nitrogen atom form a pyrrolidine ring, or $R'_3$ is —$(CH_2)_m$-Q, m is 0 and Q is a tropanyl ring, then at least -one of $R_4$ and $R_5$ is other than hydrogen;

(iii) when A is a group of Formula III, Ar is phenyl, and $R_1$, $R_2$, $R_4$, $R_5$, $R_6$ and $R_7$ are hydrogen, then $R'_3$ is other than diisopropylaminoethyl, diethylaminoethyl and N-methyl-4-piperidyl;

(iv) when A is a group of formula III, Ar is phenyl, $R_1$, $R_4$, $R_5$, $R_6$ and $R_7$ are hydrogen, and $R_2$ is p-methyl or p-methoxy, then $R'_3$ is other than N-methyl-4-piperidyl;

(v) when A is a group of Formula III, Ar is phenyl, $R_1$ and $R_2$ together form benzo, and $R_4$, $R_5$, $R_6$ and $R_7$ are hydrogen, then $R'_3$ is other than dimethylaminoethyl and diethylaminoethyl;

(vi) when A is a group of Formula IV, and Ar is phenyl, then at least one of $R_4$, $R_5$, $R_6$ and $R_7$ is other than hydrogen;

(vii) when A is a group of Formula V, Ar is phenyl, $R_4$, $R_5$, $R_6$, $R_7$, $R_8$ and $R_9$ are hydrogen, $R'_3$ is —$(CH_2)_n NR_{10}R_{11}$, and $R_{10}$ and $R_{11}$ are lower alkyl, then $R_{10}$ and $R_{11}$ contain together at least six carbon atoms; and (viii) when A is a group of Formula V, Ar is phenyl, $R'_3$ is —$(CH_2)_m$-Q, and m is 0, then at least one of $R_4$, $R_5$, $R_6$, $R_7$, $R_8$ and $R_9$ is other than hydrogen.

One subgroup of compounds of Formula I is comprised of arylcyclopropane carboxylic esters of the general Formula I(II) (i.e. where the group A in Formula I is a group of Formula II above):

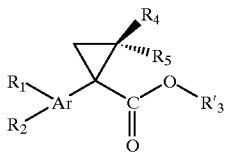

I(II)

wherein Ar, $R_1$, $R_2$, $R'_3$, $R_4$ and $R_5$, including provisions (i) and (ii), are as defined above.

In a more limited group of arylcyclopropane carboxylic esters within this subgroup, when $R'_3$ is —$(CH_2)_n NR_{10}R_{11}$, $R_{10}$ and $R_{11}$ are lower alkyl of together at least six carbon atoms.

In another limited group of compounds within this subgroup, at least one of $R_4$ and $R_5$ is other than hydrogen.

Another subgroup of compounds of Formula I is comprised of arylcyclobutane carboxylic esters of the general Formula I(III) (i.e. where the group A in Formula I is a group of Formula III above):

I(III)

wherein Ar, $R_1$, $R_2$, $R'_3$, and $R_4$ to $R_7$, including provisions (iii) to (v), are as defined above.

In a more limited group of arylcyclobutane carboxylic esters within this subgroup, at least one of $R_4$, $R_5$, $R_6$ and $R_7$ is other than hydrogen.

In another limited group of compounds within this subgroup, $R'_3$ is —$(CH_2)_m$-Q, m is 0 or 1, and Q is a saturated azabicyclic ring.

In yet another limited group of compounds within this subgroup, $R'_3$ is —$(CH_2)_m$-Q, and m is 1.

In still another limited group of compounds within this subgroup, when $R'_3$ is —$(CH_2)_n NR_{10}R_{11}$, $R_{10}$ and $R_{11}$ are lower alkyl of together at least six carbon atoms.

Another subgroup of compounds of Formula I is comprised of arylcyclopentane carboxylic esters of the general Formula I(IV) (i.e. where the group A in Formula I is a group of Formula IV above):

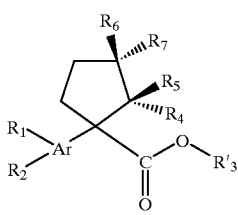

I(IV)

wherein Ar, $R_1$, $R_2$, $R'_3$, and $R_4$ to $R_7$, including provision (vi), are as defined above.

In a more limited group of arylcyclopentane carboxylic esters within this subgroup, when $R'_3$ is —$(CH_2)_nNR_{10}R_{11}$, $R_{10}$ and $R_{11}$ are lower alkyl of together at least six carbon atoms.

Yet another subgroup of compounds of Formula I is comprised of arylcyclohexane carboxylic esters of the general Formula I(V) (i.e. the group A in Formula I is a group of Formula V above):

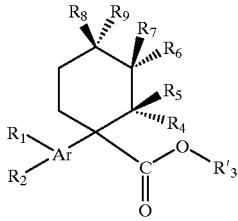

I(V)

wherein Ar, $R_1$, $R_2$, $R'_3$, and $R_4$ to $R_9$, including provisions (vii) and (viii), are as defined above.

In a more limited group of arylcyclohexane carboxylic esters within this subgroup, at least one of $R_4$, $R_5$, $R_6$, $R_7$, $R_8$ and $R_9$ is other than hydrogen.

In another limited group of compounds within this subgroup, when $R'_3$ is —$(CH_2)_nNR_{10}R_{11}$, $R_{10}$ and $R_{11}$ are lower alkyl of together at least six carbon atoms.

In another aspect, the present invention provides the compounds having the general Formula I above for therapeutical use, particularly for antagonizing muscarinic receptors, and especially for the treatment of urinary incontinence related disorders, or for the treatment of irritable bowel syndrome (IBS).

In still another aspect, the present invention provides a pharmaceutical composition comprising one or more compounds of the general Formula I above as the active ingredient, preferably together with a pharmaceutically acceptable carrier and, if desired, other pharmacologically active agents.

In yet another aspect, the present invention provides a method of treating a living body suffering from a disorder related to urinary incontinence, which method comprises the step of administering to the said living body an effective amount of a compound having the general Formula IA:

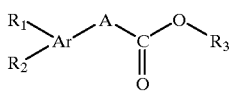

IA wherein:
A is an optionally substituted cycloalkane ring having 3 to 6 carbon atoms and attached at a single ring carbon atom thereof, Ar is phenyl or heteroaryl having 5 or 6 ring members, $R_1$, and $R_2$ independently are hydrogen, lower alkyl, lower alkoxy, halo, hydroxy, trifluoromethyl, nitro or amino, or $R_1$ and $R_2$ together form lower alkylenedioxy or optionally substituted benzo, and $R_3$ is (i) —$(CH_2)_nNR_{10},R_{11}$, in which n is 2 or 3 and $R_{10}$ and $R_{11}$ each are lower alkyl or $R_{10}$ and $R_{11}$ together with the nitrogen atom form a saturated azacyclic or azabicyclic ring system; or (ii) —$(CH_2)_m$-Q, in which m is 0 or 1 and Q is the residue of a saturated azacyclic or azabicyclic ring system coupled via a carbon atom thereof; or a pharmacologically acceptable salt thereof.

The cycloalkane ring A may be substituted at one or more ring carbons (mono- or di-substituted at each carbon), preferably with a substituent or substituents independently selected from lower alkyl, lower alkoxy, lower alkoxy-lower alkyl, cycloalkyl, lower alkenyl, lower hydroxyalkyl, benzyloxy-lower alkyl, trifluoromethyl, hydroxy, oxo or spiro-coupled lower alkylene or lower alkylenedioxy.

Preferably, the group A in Formula IA is a group of the general Formula II, III, IV or V:

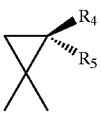

II

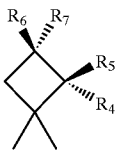

III

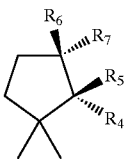

IV

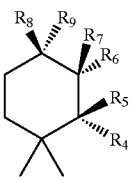

V wherein $R_4$, $R_5$, $R_6$, $R_7$, $R_8$ and $R_9$ independently are hydrogen, lower alkyl, lower alkoxy, lower alkoxy-lower alkyl, cycloalkyl, lower alkenyl, lower hydroxyalkyl, benzyloxy-lower alkyl, trifluoromethyl or hydroxy, or either $R_4$ and $R_5$ or $R_6$ and $R_7$ or $R_8$ and $R_9$ together form lower alkylene, lower alkylenedioxy or oxo.

In another aspect, the present invention provides a method of treating a living body suffering from a disorder related to irritable bowel syndrome (IBS), which method comprises the step of administering to the said living body an effective amount of a compound having the general Formula IA as defined above.

In still another aspect, the present invention provides a pharmaceutical composition for treating a disorder related to urinary incontinence, which composition comprises one or more compounds of the general Formula IA above as the active ingredient, preferably together with a pharmaceutically acceptable carrier and, if desired, other pharmacologically active agents.

In yet another aspect, the present invention provides a pharmaceutical composition for treating irritable bowel syndrome (IBS), which composition comprises one or more compounds of the general Formula IA above as the active ingredient, preferably together with a pharmaceutically acceptable carrier and, if desired, other pharmacologically active agents In another aspect, the present invention provides the use of the compounds having the general Formula IA above for the manufacture of a medicament for the treatment of urinary incontinence related disorders.

In a further aspect, the present invention provides the use of the compounds having the general Formula IA above for the manufacture of a medicament for the treatment of irritabel bowel syndrome (IBS).

In still another aspect, the present invention provides processes for preparing compounds having the general Formula I above.

DETAILED DESCRIPTION OF THE INVENTION

In the compounds having the general Formulae I and IA as defined above, the term lower alkyl, separately and in combinations (as well as in alkylene), is meant to include straight and branched, saturated hydrocarbon groups having from one to six carbon atoms, particularly from one to five, and preferably from one to four carbon atoms. Exemplary alkyl groups are methyl, ethyl, n-propyl, iso-propyl, n-butyl, n-pentyl, n-hexyl and isomeric forms thereof.

The term lower alkenyl, separately and in combinations, is meant to include straight and branched hydrocarbon groups having from two to six carbon atoms, particularly from two to five, and preferably from two to four carbon atoms, and containing one or more unsaturations. Exemplary alkenyl groups are ethenyl, propenyl, butenyl, pentenyl, hexenyl, methylpropenyl, ethylbutenyl and isomeric forms thereof.

The term lower alkoxy, separately and in combinations, is meant to include straight and branched, saturated alkoxy groups having from one to six carbon atoms, particularly from one to five, and preferably from one to four carbon atoms. Exemplary alkoxy groups are methoxy, ethoxy, n-propyloxy, iso-propyloxy, n-butyloxy, n-pentyloxy, n-hexyloxy and isomeric forms thereof.

Cycloalkyl is preferably $C_{3-8}$cycloalkyl, such as cyclopropyl, cyclobutyl, cyclopentyl, cyclohexyl, cycloheptyl, cyclooctyl.

Exemplary heteroaryl groups are thiophene, furan, thiazole, isothiazole, oxazole, isoxazole, pyridine, pyrazine, pyrimidine, pyridazine. Preferred heteroaryl groups are 2- or 3-thienyl, 2- or 3-furanyl, and 2-, 3- or 4-pyridine.

Halo includes fluoro, chloro, bromo and iodo, and is preferably fluoro, chloro or bromo.

Lower alkylenedioxy is preferably methylenedioxy.

Benzo is preferably 2,3-benzo or 3,4-benzo. When benzo is substituted, it may be substituted in one or more of the ortho-, metha- or para-positions. Preferably, it is di- or mono-substituted, more preferably mono-substituted.

When $R'_3$ or $R_3$ comprises a saturated azacyclic or azabicyclic ring system, the nitrogen atom thereof will have tertiary nature, either by being a bridge end or by substitution, preferred N-substituents being lower alkyl and lower alkenyl.

Exemplary azacyclic and azabicyclic rings are piperidine, pyrrolidine, azanorbornane, azacycloheptane, quinuclidine, isoquinuclidine, tropane, azabicyclo[3.2.1]octane, azabicyclo[2.2.1]heptane, 2, azabicyclo([3.2.1]octane, azabicyclo[3.3.0]octane, azabicyclo[3.2.2]nonane, azabicyclo[3.3.1]nonane.

The azacyclic or azabicyclic rings may be mono- or independently di-substituted at a carbon atom in any position by lower alkyl, lower alkenyl, halo, lower alkoxy or hydroxy, preferably by methyl, methoxy or hydroxy.

When $R'_3$ or $R_3$ is $-(CH_2)_nNR_{10}R_{11}$, n is preferably 2, and, when $R'_3$ or $R_3$ is $-(CH_2)_m-Q$, m=0 and Q is an azabicyclic ring, the nitrogen atom of the azabicyclic ring is preferably spaced from the coupling carbon atom by one carbon atom.

When $R_4$, $R_5$, $R_6$, $R_7$, $R_8$ and $R_9$ are separate groups, they are preferably selected from hydrogen, lower alkyl, lower alkoxy, methoxymethyl, benzyloxymethyl, ethenyl, propenyl and trifluoromethyl. In case $R_4$ and $R_5$, $R_6$ and $R_7$, or $R_8$ and $R_9$ together form lower alkylene or lower alkylenedioxy, they are preferably selected from dimethylene, trimethylene and ethylenedioxy.

In preferred subgroups of the compounds of formula I and IA, respectively:

Ar is phenyl, 2- or 3-thienyl, 2- or 3-furanyl or 2-, 3- or 4-pyridine; and/or $R_1$ and $R_2$ are independently hydrogen, fluoro, chloro, bromo, $C_{1-4}$alkyl, $C_{1-4}$alkoxy, methoxymethyl, phenoxymethyl, vinyl, allyl, trifluormethyl; and/or $R_4$, $R_5$, $R_6$, $R_7$, $R_8$ and $R_9$ are independently hydrogen, $C_{1-4}$alkyl, $C_{1-4}$alkoxy, methoxymethyl, benzyloxymethyl, vinyl, allyl, trifluoromethyl, or either $R_4$ and $R_5$, or $R_6$ and $R_7$, or $R_8$ and $R_9$ together form dimethylene, trimethylene, tetramethylene or ethylenedioxy.

The general Formulae I and IA include the enantiomeric and racemic forms. The compounds of Formulae I and IA may also be in the form of salts suitable for pharmacological use. They may form salts with physiologically acceptable acids, organic and inorganic, and the invention comprises the free bases as well as the salts thereof. Examples of such salts include the hydrochloride, hydrobromide, hydrogen fumarate and the like.

Exemplary compounds of Formulae I and IA include:
2-(Diisopropylamino)ethyl 1-phenyl-2-trans-methoxymethylcyclopropanecarboxylate;
3-quinuclidinyl 1-phenylcyclopropanecarboxylate;
2-(diisopropylamino)-ethyl 1-phenyl-cis-2-methoxymethylcyclopropanecarboxylate;
2-(diisopropylamino)ethyl 1-phenyl-3,3-dimethylcyclobutane-carboxylate;
3-quinuclidinyl 1-phenylcyclobutanecarboxylate;
2-(diisopropylamino)ethyl 1-phenyl-3-cis-methylcyclobutanecarboxylate;
2-(diisopropylamino)ethyl 1-phenylcyclopentanecarboxylate;
3-quinuclidinyl 1-phenylcyclopentanecarboxylate;
2-(diisopropylamino)ethyl 1-phenylcyclohexanecarboxylate; and
3-quinuclidinyl 1-phenylcyclohexanecarboxylate.

The compounds of the general Formulae I and IA may be prepared by or in analogy with conventional methods, and especially according to or in analogy with the following methods a) and b).

Method a:

A compound of the general Formula VI:

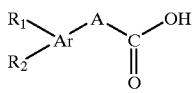

VI wherein $R_1$, $R_2$, A and Ar are as defined above, or a reactive derivative thereof where the carboxyl group has been activated,
is reacted with a compound of the general Formula VIIA:

HO—$R_3$     VIIa wherein $R_3$ is as defined above, or with a compound of the general Formula VIIIa:

Cl—$R_3$     VIIIa wherein $R_3$ is as defined above, in the presence of a strong base.

Method b:

In a compound of the general formula IXa:

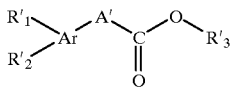

IXa wherein $R_3$ is as defined above, and A', $R'_1$ and $R'_2$ represent A, $R_1$ and $R_2$, respectively, as defined above, or a group that can be converted to A, $R_1$ and $R_2$, respectively,
at least one of A', $R'_1$ and $R'_2$ is converted to a group A, $R_1$ and $R_2$, respectively.

The conversion of the group A' to a group A usually comprises converting one or more substituents on the cycloalkane ring. Particularly, A' is a group of the general Formula IIa, IIIa, IVa or Va:

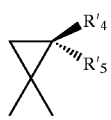

IIa

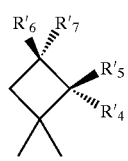

IIIa

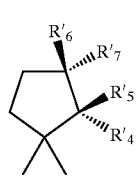

IVa

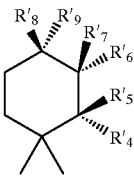

Va wherein $R'_4$, $R'_5$, $R'_6$, $R'_7$, $R'_9$ and $R'_9$ represent $R_4$, $R_5$, $R_6$, $R_7$, $R_8$ and $R_9$, respectively, or a group that can be converted to $R_4$, $R_5$, $R_6$, $R_7$, $R_8$ and $R_9$, respectively, one or more of groups $R'_4$, $R'_5$, $R'_6$, $R'_7$, $R'_8$ and $R'_9$ are converted to a group $R_4$, $R_5$, $R_6$, $R_7$, $R_8$ and $R_9$, respectively.

When method a) above is carried out by reacting a compound of Formula VI with a compound of Formula VIIa, the compound of Formula VI is preferably transformed to a reactive derivative, such as the anhydride or acid chloride. In the latter case (which is illustrated further in, for example, Example 4 below), the reaction may be carried out in an inert organic solvent or mixture of solvents, such as benzene or toluene. A suitable temperature range for the reaction is between between room temperature and about 100° C. The resulting product may be isolated by conventional procedures.

An acid chloride of a compound of Formula VI above may be prepared by reacting the compound VI with thionyl chloride. The resulting acid chloride does not need to be isolated but may be added directly to the reaction mixture.

The reaction of a compound of Formula VI with a compound of Formula VIIIa (which is further illustrated in, for example, Example 7 below) may be carried out in a dipolar aprotic organic solvent or mixture of solvents, such as dimethylformamide, acetonitril or dimethyl sulphoxide. As strong base, sodium hydride or potassium tert.-butylate may be used. A suitable temperature range for the reaction is between about 0 and about 100° C. The resulting product may be isolated by conventional procedures.

The reaction between a compound of Formula VI in acid form and a compound of Formula VIIa is carried out in the presence of a dehydrating agent, preferably a carbodiimide, such as dicyclohexylcarbodiimide (DCC) and a base as catalyst.

In method b) (which is further illustrated in, e.g., Example 9 below), for example, a compound of Formula I or IA having a hydroxy-containing substituent may be obtained by hydrogenating a corresponding benzyloxy compound. Method b) also includes the conversion of one or more of the groups $R_4$, $R_5$, $R_6$, $R_7$, $R_8$ and $R_9$ to another group or groups $R_4$, $R_5$, $R_6$, $R_7$, $R_8$ and $R_9$, respectively, for example the conversion of a nitro group to an amino group by hydrogenation, or the reduction of an oxo group to a hydroxy group.

When in Formula I or IA, the group A is a group of Formula II as defined above, a trans-substituted starting material of Formula VI may be prepared by reacting a corresponding arylacetic ester with a suitable chloroepoxyalkane to form a compound of Formula II having a hydroxyl-containing trans-substituent, and optionally etherifying the hydroxyl group, route A (see e.g. Example 1 below). To prepare a cis-substituted starting material of Formula VI, a corresponding arylnitrile is substituted for the arylacetic ester in the above procedure, route B (see e.g. Example 3 below). The above reaction routes A and B are outlined in Reaction Scheme I provided at the end of the description.

An arylcyclopropane carboxylic acid of Formula VI may be converted to another arylcyclopropane carboxylic acid of Formula VI by converting one or more substituents on the cyclopropane ring, such as substituents $R_4$ or $R_5$ as defined above.

When the group A in Formula I or IA is a group of Formula III, starting materials of Formula VI may e.g. be prepared by any of routes A to E shown in Reaction Scheme II.

In route A, an arylacetonitrile is reacted with a 1,3-dibromopropane to give an arylcyclobutanecarbonitrile, which is then hydrolyzed to form the arylcyclobutanecarboxylic acid of Formula VI (illustrated in Examples 9 to 26 below).

In routes B and C, an arylacetonitrile is reacted with a di-O-p-toluenesulfonyl-1,3-propanediol (route B) or 3-bromo-o-p-toluenesulfonyl-1-propanol (route C) to give a 1-phenylcyclobutanecarbonitrile, which is then hydrolyzed to form the arylcyclobutanecarboxylic acid of Formula VI. (Route B is illustrated in Examples 27–28, and route C in Examples 29–31 below).

In route D, an arylacetic ester is reacted with a 1,3-dibromopropane to give a 1-phenylcyclobutanecarboxylic ester, which is then hydrolyzed to form the arylcyclobutanecarboxylic acid of Formula VI (illustrated in Examples 32–33 below).

In route E, a 1-cyano-1-phenyl-3-oxycyclobutane is reacted with an alkyltriphenylphosphoniumbromide (Wittig reaction) to give a 1-phenyl-3-alkylenecyclobutanecarbonitrile, which is then hydrolyzed to form the arylcyclobutanecarboxylic acid of Formula VI (illustrated in Example 34).

An arylcyclobutanecarboxylic acid of Formula VI may be converted to another arylcyclobutanecarboxylic acid of Formula VI by converting one or more substituents on the cyclobutane ring, such as $R_1$, $R_2$, $R_4$, $R_5$, $R_6$ or $R_7$ (illustrated in Example 35) as defined above.

When the group A in Formula I or IA is a group of Formula IV, starting materials of Formula VI may e.g. be prepared by route A or B shown in Reaction Scheme III.

In route A, an arylacetonitrile is reacted with a 1,4-dibromobutane to give an arylcyclobutanecarbonitrile, which is then hydrolyzed to form the arylcyclopentanecarboxylic acid of Formula VI (illustrated in Examples 94 and 95 below).

In route B, an arylacetonitrile is reacted with a di-O-p-toluenesulfonyl-1,4-butanediol to give a 1-phenylcyclobutanecarbontrile, which is then hydrolyzed to form the arylcyclopentanecarboxylic acid of Formula VI (illustrated in Example 96 below).

An arylcyclopentanecarboxylic acid of Formula VI may be converted to another arylcyclopentanecarboxylic acid of Formula VI by converting one or more substituents on the cyclopentane ring, such as $R_1$, $R_2$, $R_4$, $R_5$, $R_6$ or $R_7$ as defined above.

When the group A in Formula I or IA is a group of Formula V, starting materials of Formula VI may e.g. be prepared by any of routes A to C shown in Reaction Scheme IV.

In route A, an arylcyclohexanonecarbonitrile is reduced to the corresponding alcohol, which is then alkylated and hydrolyzed to form an arylcyclohexane- carboxylic acid of Formula VI (illustrated in Example 113 below).

In route B, the oxo group of an arylcyclohexanonecarbonitrile is first protected by rection with ethyleneglycol. The nitrile is then hydrolyzed to carboxylic acid, whereupon the oxo group is deprotected to form an arylcyclohexanecarboxylic acid of Formula VI (illustrated in Example 114 below).

In route C, an arylacetonitrile is reacted with a di-O-p-toluenesulfonyl-1,5-pentanediol to give a 1-phenylcyclohexanecarbontrile, which is then hydrolyzed to form an arylcyclohexanecarboxylic acid of Formula VI (illustrated in Examples 115 and 116 below).

An arylcyclohexanecarboxylic acid of Formula VI may be converted to another arylcyclohexanecarboxylic acid of Formula VI by converting one or more substituents on the cyclohexane ring, such as $R_1$, $R_2$, $R_4$, $R_5$, $R_6$, $R_7$, $R_8$ or $R_9$ as defined above.

The racemic compounds of the general Formulae I and IA may be resolved using known methods, such as various resolving acids. Crystallization of a resolving acid salt of compounds of the general Formulae I and IA may be effected in any suitable conventional inert organic solvent, and preferably at a temperature from the boiling point of the solvent to −20° C. Exemplary solvents are ethanol, 1-propanol, 2-propanol, acetone, diethyl ether and ethyl acetate. Water and mixtures of solvents may also be employed.

The separation of racemates can also be achieved by various chromatographic techniques, such as separation of diastereomeric mixtures, separation on chiral stationary phases or with chiral counter ion in the mobile phase.

All the above described methods, including the resolution of racemates, may optionally be carried out in the presence of a catalyst known to be useful therein.

The compounds of the invention are generally characterized by the pharmacological activity stated above, making them useful for counteracting the indicated physiological abnormalities in a living human or animal body. Effective quantities of a pharmacologically active compound of the invention may be administered to a living human or animal body in any one of various ways, e.g. orally as in capsules or tablets, parenterally in the form of sterile solutions, suspensions, emulsions, pellet implantation or by pumps. Among routes of parenteral administration are intravenous, sublingual, subcutaneous, intramuscular, intraperitoneal, intradermal, intravesical, intraurethral and intranasal administration. Other modes of administration are vaginal, rectal and topical administrations, e.g. in the form of ointments, suppositories, powders, patches, sprays and intravaginal devices.

Pharmaceutical formulations are usually prepared from a predetermined quantity of one or more of the compounds of the Formulae I or IA above. Such formulations may take the form of powders, syrups, suppositories, ointments, solutions, pills, capsules, pellets or tablets, suspensions, emulsions, oil solutions, etc. with or without, but preferably with any one of a large variety of pharmaceutically acceptable vehicles or carriers.

When in a mixture with a pharmaceutical vehicle or carrier, the active ingredient usually comprises from about 0.01 to about 75%, normally about 0.05 to about 15% by weight of the composition. Carriers such as starch, sugar, talc, commonly used synthetic and natural gums, water and the like may be used in such formulations. Binders, such as polyvinylpyrrolidone, and lubricants, such as sodium stearate, may be used to form tablets. Disintegrating agents such as sodium carbonate may also be included in tablets.

Although relatively small quantities of the active materials of the invention, even as low as e.g. 0.5 milligram, may be used in cases of administration to subjects having a relatively low body weight, unit dosages are preferably 2 milligrams or above, and preferably 10, 20, 50 or 100 milligrams, or even higher depending, of course, upon the subject treated and the particular result desired, as will be apparent to one skilled in the art. Broader ranges would be from 1 to 1000 milligrams per unit dose.

The present compounds of Formulae I and IA may thus be administered in a quantity of 1 to 1000 milligrams, preferred ranges being 2 to 250 milligrams per day per subject or patient divided into one to four doses over a suitable period and depending upon the subject and the type of subject being treated.

The following examples are intended to illustrate but not to limit the scope of the invention. The structures of the compounds prepared were confirmed by NMR and elemental or titrimetric analyses. The NMR data were recorded using a JEOL 270 MHz or a Varian 500 MHz instrument. Elemental analyses were performed by Mikrokemi AB, Uppsala, Sweden. Melting points, when given, were determined on a Buchi 530 apparatus and are uncorrected.

I. Arylcyclopropane carboxylic esters

EXAMPLE 1

Starting Material
1-Phenyl-2-trans-methoxymethylcyclopropanecarboxylic acid

Ethyl phenylacetate (0.10 mol) dissolved in DMF (80 mL) was added to NaH (60% dispersion in mineral oil, 0.10 mol) at ambient temperature during 30 min. The mixture was cooled to 0° C. and epichlorohydrin (0.10 mol) in DMF (20 mL) was added during 30 min. Additional NaH (0.10 mol) was used. The reaction mixture was partitioned between toluene and $H_2O$. The organic layer was washed 3 times with 1 M NaOH, dried ($MgSO_4$) and evaporated. Purification on silica gel using petroleumether-EtOAc 90:10 yielded 2.8 g (13%) of ethyl 1-phenyl-2-trans-hydroxymethylcyclopropanecarboxylate.

A solution of methyl iodide (10 mmol) and ethyl 1-phenyl-2-trans-hydroxymethylcyclopropanecarboxylate (5 mmol) in DMF (5 mL) was added to NaH (60%, 15 mmol) at ambient temperature during 15 min. After 1 h of stirring, the reaction mixture was partitioned between toluene and $H_2O$. The organic layer was dried ($MgSO_4$) and evaporated to yield 0.8 g. Chromatography on silica gel using hexane-EtOAc 90:10 yielded 0.47 g (40%); $^1$H NMR ($CDCl_3$) δ 1.15 (t, 3H), 1.22 (dd, 1H), 1.75 (dd, 1H), 2.17 (m, 1H), 2.91 (dd, 1H), 3.06 (dd, 1H), 3.19 (s, 3H), 4.07 (m, 2H), 7.32 (m, 5H).

The afforded ethyl 1-phenyl-2-trans-methoxymethylcyclopropanecarboxylate (1.9 mmol) was refluxed with KOH (10 mmol) in ethyleneglycol (5 mL) for 3 h, allowed to cool to room temperature, toluene and $H_2O$ were added and the layers were separated. The aqueous layer was acidified and extracted with toluene, whereupon the organic layer was dried ($MgSO_4$) and concentrated to provide the title carboxylic acid.

EXAMPLE 2

Starting Material
1-Phenyl-2-trans-benzyloxymethylcyclopropanecarboxylic acid

Ethyl 1-phenyl-2-trans-hydroxymethylcyclopropanecarboxylate (6.8 mmol), obtained in Example 1 above, was dissolved in DMF (10 mL) together with benzylchloride (8 mmol) and added to NaH (60% dispersion in mineral oil, 10 mmol) at ambient temperature during 15 min. After 1 h of stirring, excess hydride was decomposed by addition of EtOH and the reaction mixture was partitioned between toluene and $H_2O$. The organic layer was dried ($MgSO_4$) and evaporated. The residue was chromatographed on silica gel using toluene-EtOAc 19:1 as eluent to yield 1.0 g (47%); $^1$H NMR ($CDCl_3$) δ 1.16 (t, 3H), 1.22 (dd, 1H), 1.75 (dd, 1H), 2.24 (m, 1H), 2.95 (dd, 1H), 3.27 (dd, 1H), 4.07 (m, 2H), 4.30 (m, 2H), 7.32 (m, 10H).

The afforded ethyl 1-phenyl-2-trans-benzyloxymethylcyclopropanecarboxylate (3.2 mmol) was hydrolysed in a similar way as in Example 1 to produce the title compound.

EXAMPLE 3

Starting Material
1-Phenyl-2-cis-methoxymethylcyclopropanecarboxylic acid

A solution of phenylacetonitrile (30 mmol) and epichlorohydrin (30 mmol) in DMF (40 mL) was added to NaH (60% dispersion in mineral oil, 0.10 mol) at 0° C. during 15 min. The temperature was allowed to rise to room temperature and methyl iodide (30 mmol) was added. After 30 min of stirring, $H_2O$ was added and the mixture was extracted with toluene. The organic layer was dried ($Na_2SO_4$) and evaporated. Chromatography on silica gel using hexane-EtOAc 90:10 as eluent yielded 1-phenyl-2-cis-methoxymethylcyclopropanecarbonitrile that was hydrolysed in a similar way as in Example 1. The afforded crude product was recrystallised from toluene-hexane to yield 1.1 g (28%) of the title compound; $^1$H NMR ($CDCl_3$) δ 1.44 (dd, 1H), 1.68 (dd, 1H), 1.95 (m, 1H), 3.38 (s, 3H), 3.63 (t, 1H), 3.56 (dd, 1H), 7.34 (m, 5H), 10–12 (br, 1H).

EXAMPLE 4

2-(Diisopropylamino)ethyl 1-phenyl-2-trans-methoxymethylcyclopropanecarboxylate hydrochloride 1-Phenyl-2-trans-methoxymethylcyclopropanecarboxylic acid (1.9 mmol), obtained in Example 1, was refluxed with $SOCl_2$ (5 mL). After 0.5 h, the reaction mixture was evaporated and the residue was dissolved in toluene. 2-Diisopropylaminoethanol (3.8 mmol) was added and the mixture was stirred at room temperature overnight. The reaction mixture was then filtered through a layer of silica gel and evaporated. The residue was dissolved in $Et_2O$ and HCl (g)/$Et_2O$ was added whereby the product crystallized to yield 0.22 g (31%) of the title compound; mp 116–118° C.; $^1$H NMR ($CD_3OD$) δ 1.20 (m, 12H), 1.34 (dd, 1H), 1.73 (dd, 1H), 2.18 (m, 1H), 2.78 (dd, 1H), 3.16 (s, 3H), 3.22 (dd, 1H), 3.36 (t, 2H), 3.57 (m, 2H), 4.34 (m, 2H), 7.37 (m, 5H). Anal. ($C_{20}H_{31}NO_3.HCl$) C, H, N.

EXAMPLE 5

2-(Diisopropylamino)ethyl 1-phenyl-2-trans-benzyloxymethylcyclopropanecarboxylate hydrochloride The title compound was prepared in analogous manner to that in Example 4 from the starting material prepared in Example 2. The reaction with $SOCl_2$ was performed at room temperature for 1 h. The yield was 0.5 g (35%); mp 117–120 ° C.; $^1$H NMR ($CD_3OD$) δ 1.20 (m, 12H), 1.33 (dd, 1H), 1.75 (dd, 1H), 2.23 (m, 1H), 2.86 (t, 1H), 3.28–3.42 (m, 3H), 3.55 (m, 2H), 4.20–4.40 (m, 4H), 7.20–7.50 (m, 10H). Anal. ($C_{26}H_{35}NO_3.HCl$) C, H, N.

EXAMPLE 6

3-Quinuclidinyl 1-phenylcyclopropanecarboxylate hydrochloride

The title compound was prepared in analogous manner to that in Example 4. The 1-phenylcyclopropanecarbonyl chloride obtained after the chlorination step was reacted with 3-quinuclidinol at 80° C. for 21 h. The reaction mixture was filtered and chromatographed on silica gel using toluene- Et₃N 95:5 as eluent. The yield was 0.76 g (40%); mp 229–233° C.; ¹H NMR (D₂O) δ 1.42–1.48 (m, 2H), 1.72–1.78 (m, 2H), 1.81–1.98 (m, 3H), 2.10 (m, 1H), 2.40 (m, 1H), 3.14 (m, 1H), 3.25–3.41 (m, 4H), 3.71 (m, 1H), 5.17 (m, 1H), 7.44 (m, 1H), 7.49 (m, 2H), 7.55 (m, 2H) Anal. (C₁₇H₂₁NO₂.HCl) C, H, N.

EXAMPLE 7

2-(Diisopropylamino)ethyl 1-phenyl-cis-2-methoxymethylcyclopropanecarboxylate hydrochloride A solution of 1-phenyl-cis-2-methoxymethylcyclopropane acid (1.5 mmol), obtained in Example 3, in DMF (3 mL) was added to NaH (60% dispersion in mineral oil, 20 mmol, washed twice with hexane) at ambient temperature. After 30 min, N,N-diisopropyl-2-chloroethylamine (1.8 mmol) was added. After 2 h, the reaction mixture was partitioned between H₂O and toluene. The organic layer was passed through a short layer of silica gel using toluene-EtOAc 90:10 as eluent. The pooled fractions were concentrated, dissolved in Et₂O-hexane and HCl (g)/Et₂O was added whereby the product, the title compound, crystallised. The yield was 0.20 g (56%); mp 46–50° C.; ¹H NMR (CD₃OD) δ 1.17 (m, 12H), 1.38 (dd, 1H), 1.71 (dd, 1H), 2.03 (m, 1H), 3.33 (m, 2H), 3.37 (s, 3H), 3.55 (m, 3H), 3.82 (dd, 1H), 4.35 (m, 2H) and 7.34 (m, 5H). Anal. (C₂₀H₃₁NO₃.HCl) C, H, N.

EXAMPLE 8

2-(Diisopropylamino)ethyl 1-phenyl-2-trans-hydroxymethylcyclopropanecarboxylate hydrochloride 2-(Diisopropylamino)ethyl 1-phenyl-2-trans-benzyloxymethylcyclopropanecarboxylate (0.32 g, 0.79 mmol), obtained in Example 5, was dissolved in HOAc (10 mL). Palladium (10%) on charcoal (50 mg) was added and the mixture was hydrogenated at atmospheric pressure for 16 h. The catalyst was then filtered off and the solvent was evaporated. The residue was partitioned between toluene and 1 M NaOH. The aqueous layer was extracted several times with toluene. The combined organic layers were dried (MgSO₄) and concentrated to afford the free base that was dissolved in isopropanol and Et₂O, and HCl (g)/Et₂O was added dropwise to yield 0.15 g (54%) of the title compound; mp 105–107° C.; ¹H NMR (CD₃OD) δ 1.20 (m, 12H), 1.32 (dd, 1H), 1.73 (dd, 1H), 2.16 (m, 1H), 3.16 (d, 2H), 3.35 (t, 2H), 3.57 (m, 2H), 4.35 (m, 2H), 7.35 (m, 5H). Anal. (C₁₉H₂₉NO₃-HCl) C, H, N.

II. Arylcyclobutane carboxylic esters

EXAMPLE 9

Starting Material 1-(2-bromophenyl)cyclobutanecarboxylic Acid

NaH (80% dispersion in mineral oil, 127 mmol) was washed several times with n-pentane and suspended in DMF (50 mL). A mixture of 2-bromophenylacetonitrile (51 mmol) and 1,3-dibromopropane (51 mmol) in DMF (50 mL) was added dropwise to the ice-cold mixture. The reaction mixture was stirred at room temperature for 3 h. Excess hydride was then decomposed by the cautious addition of H₂O. Extraction with toluene, drying of the organic layer (MgSO₄) and evaporation of the solvent afforded 1-(2-bromophenyl)-cyclobutanecarbonitrile that was refluxed with KOH (210 mmol) in ethyleneglycol (50 mL) for 4 h. The resulting solution was then allowed to cool to room temperature, toluene and H₂O were added and the layers were separated. The aqueous layer was acidified and extracted with EtOAc. The organic layer was dried (MgSO₄) and concentrated to provide the desired product. The yield was 8.5 g (65%); ¹H NMR (CDCl₃) δ 1.80–1.93 (m, 1H), 2.20–2.40 (m, 1H), 2.54–2.65 (m, 2H), 2.86–2.96 (m, 2H), 7.07–7.15 (m, 1H), 7.29–7.37 (m, 2H), 7.53 (d, 1H)

EXAMPLE 10

Starting Material 1-(4-Bromophenyl)cyclobutanecarboxylic Acid

The title compound was prepared in an analogous manner to that in Example 9 from 4-bromophenylacetonitrile and 1,3-dibromopropane. The yield was 6 g (46%); ¹H NMR (CDCl₃) δ 1.79–1.94 (m, 1H), 2.00–2.17 (m, 1H), 2.42–2.53 (m, 2H), 2.78–2.88 (m, 2H), 7.17 (d, 2H), 7.45 (d, 2H).

EXAMPLE 11

Starting Material 1-(3,4-Methylenedioxyphenyl)cyclobutanecarboxylic Acid

The title compound was prepared in an analogous manner to that in Example 9 from 3,4-methylenedioxyphenylacetonitrile and 1,3-dibromopropane. 2.1 eq of NaH and 1.1 eq of 1,3-dibromopropane were used. The mixture of 3,4-methylenedioxyphenylacetonitrile and 1,3-dibromopropane was added at 0° C. The afforded 1-(3,4-methylenedioxyphenyl)cyclobutanecarbonitrile was purified by chromatography on silica gel using petroleum ether-EtOAc 94:6 as eluent. The product (11 mmol) was then refluxed with KOH (33 mmol) in ethyleneglycol (16.6 mL) and H₂O (1.4 mL) for 7 h. The cooled mixture was extracted with Et₂O. The aqueous layer was acidified and extracted with Et₂O. The crude was chromatographed on silica gel using EtOAc-HOAc 99:1 as eluent to give the desired product. The yield was 1.1 g (26%); ¹H NMR (CDCl₃) δ 1.80–1.95 (m, 1H), 1.97–2.12 (m, 1H), 2.40–2.50 (m, 2H), 2.75–2.85 (m, 2H), 5.91 (s, 2H), 6.75–6.80 (m, 3H).

EXAMPLE 12

Starting Material

1-Phenyl-2-cis-methylcyclobutanecarboxylic Acid

The title compound was prepared in an analogous manner to that in Example 9 from phenylacetonitrile and 1,3-dibromo-1-methylpropane. The reaction with NaH was stirred overnight. The afforded 1-phenyl-2-methylcyclobutanecarbonitrile was a mixture of cis and trans isomers. The isomers were separated by chromatography on silica gel using hexane-toluene 85:15 as eluent. The yield of 1-phenyl-2-cis-methylcyclobutanecarboxylic acid was 0.83 g (14%); ¹H NMR (CDCl₃) δ 1.32 (d, 3H), 1.87 (m, 1H), 2.05 (m, 1H), 2.22 (m, 1H), 2.86 (m, 1H), 3.04 (m, 1H), 7.20–7.40 (m, 5H).

EXAMPLE 13

Starting Material

1-Phenyl-2-trans-methylcyclobutanecarboxylic Acid

Fractions containing the trans isomer afforded in the preparation of 1-phenyl-2-cis-methylcyclobutanecarboxylic acid in Example 12 above were pooled to yield 0.55 g (8.5%) of 1-phenyl-2-trans-methylcyclobutanecarboxylic acid; $_1$H NMR (CDCl$_3$) δ 0.79 (d, 3H), 1.47 (m, 1H), 2.22 (m, 1H), 2.60 (m, 1H), 2.74 (m, 1H), 3.12 (m, 1H), 7.20–7.40 (m, 5H).

EXAMPLE 14

Starting Material 1-(1-Naphthyl)cyclobutanecarboxylic Acid

The title compound was prepared in an analogous manner to that in Example 9 from 1-naphthylacetonitrile and 1,3-dibromopropane. The reaction mixture with NaH was stirred overnight. 1-(1-Naphthyl)cyclobutanecarbonitrile was refluxed with KOH overnight. The yield was 6.9 g (42%); $^1$H NMR (CDCl$_3$) δ 1.92 (m, 1H), 2.25 (m, 1H), 2.73 (m, 2H), 3.05 (m, 2H), 7.47 (m, 4H), 7.80 (m, 3H).

EXAMPLE 15

Starting Material 1-(2-Naphtyl)cyclobutanecarboxylic Acid

The title compound was prepared in an analogous manner to that in Example 9 from 2-naphthylacetonitrile and 1,3-dibromopropane. The yield was 3.0 g (44%).

EXAMPLE 16

Starting Material 1-(3-Methylphenyl)cyclobutanecarboxylic Acid

The title compound was prepared in an analogous manner to that in Example 9 from 3-methylphenylacetonitrile and 1,3-dibromopropane. The yield was 0.72 g (54%); $^1$H NMR (CDCl$_3$) δ 1.75–1.92 (m, 1H), 1.98–2.16 (m, 1H), 2.28 (s, 3H), 2.42–2.59 (m, 2H), 2.75–2.90 (m, 2H), 6.95–7.15 (m, 3H), 7.2 (d, 1H).

EXAMPLE 17

Starting Material 1-(2-Methoxyphenyl)cyclobutanecarboxylic Acid

The title compound was prepared in an analogous manner to that in Example 9 from 2-methoxyphenylacetonitrile and 1,3-dibromopropane. The yield was 3.9 g (15%); $^1$H NMR (CDCl$_3$) δ 1.85 (m, 1H), 2.20 (m, 1H), 2.50 (m, 2H), 2.80 (m, 2H), 3.80 (m, 3H), 6.84 (d, 1H), 6.96 (t, 1H), 7.22 (t, 2H).

EXAMPLE 18

Starting Material 1-(4-Methylphenyl)cyclobutanecarboxylic Acid

The title compound was prepared in an analogous manner to that in Example 9 from 4-methylphenylacetonitrile and 1,3-dibromopropane. The crude was washed with petroleumether-toluene 90:10. The yield was 82%; $^1$H NMR (CDCl$_3$) δ 1.86 (m, 1H), 2.05 (m, 1H), 2.32 (s, 3H), 2.49 (m, 2H), 2.82 (m, 2H), 7.17 (m, 4H), 9.6 (br, 1H).

EXAMPLE 19

Starting Material 1-(2-Methylphenyl)cyclobutanecarboxylic Acid

The title compound was prepared in an analogous manner to that in Example 9 from 2-methylphenylacetonitrile and 1,3-dibromopropane. The crude was washed with petroleumether-toluene 90:10. The yield was 83%; $^1$H NMR (CDCl$_3$) δ 1.85 (m, 1H), 2.21 (m, 4H), 2.55 (m, 2H), 2.84 (m, 2H), 7.07–7.23 (m, 4H), 11.0 (br, 1H).

EXAMPLE 20

Starting Material 1-(4-Fluorophenyl)cyclobutanecarboxylic Acid

The title compound was prepared in an analogous manner to that in Example 9 from 4-fluorophenylacetonitrile and 1,3-dibromopropane. The crude was washed with petroleumether-toluene 90:10 as eluent; $^1$H NMR (CDCl$_3$) δ 1.86 (m, 1H), 2.06 (m, 1H), 2.47 (m, 2H), 2.83 (m, 2H), 7.00 (m, 2H), 7.26 (m, 2H), 11.1 (br, 1H).

EXAMPLE 21

Starting Material 1-(2-Fluorophenyl)cyclobutanecarboxylic Acid

The title compound was prepared in an analogous manner to that in Example 9 from 2-fluorophenylacetonitrile and 1,3-dibromopropane. The crude was chromatographed on silica gel using petroleumether-EtOAc-HOAc 90:8:2 as eluent. The yield was 86%; $^1$H NMR (CDCl$_3$) δ 1.88 (m, 1H), 2.24 (m, 1H), 2.53 (m, 2H), 2.84 (m, 2H), 6.95–7.28 (m, 4H), 11.8 (br, 1H).

EXAMPLE 22

Starting Material 1-(3-Fluorophenyl)cyclobutanecarboxylic Acid

The title compound was prepared in an analogous manner to that in Example 9 from 3-fluorophenylacetonitrile and 1,3-dibromopropane. The yield was 70%; $^1$H NMR (CDCl$_3$) δ 1.89 (m, 1H), 2.06 (m, 1H), 2.49 (m, 2H), 2.83 (m, 2H), 6.98 (m, 3H), 7.23 (m, 1H), 10.2 (br, 1H).

EXAMPLE 23

Starting Material 1-(3-Methoxyphenyl)cyclobutanecarboxylic Acid

The title compound was prepared in an analogous manner to that in Example 9 from 3-methoxyphenylacetonitrile and 1,3-dibromopropane. The crude was washed with petroleumether-toluene 85:15. The yield was 70%; 1H-NMR (CDCl$_3$) δ 1.84 (m, 1H), 2.04 (m, 1H), 2.51 (m, 2H), 2.82 (m, 2H), 3.79 (s, 3H) 6.83 (m, 3H), 7.22 (m, 1H), 10.9 (br, 1H).

EXAMPLE 24

Starting Material 1-(4-Methoxyphenyl)cyclobutanecarboxylic Acid

The title compound was prepared in an analogous manner to that in Example 9 from 4-methoxyphenylacetonitrile and 1,3-dibromopropane. The yield was 83%; 1H-NMR (CDCl$_3$) δ 1.90 (m, 1H), 2.04 (m, 1H), 2.47 (m, 2H), 2.81 (m, 2H), 3.78 (s, 3H), 6.86 (m, 2H), 7.22 (m, 2H), 10.8 (br, 1H).

EXAMPLE 25

Starting Material 1-(2-Thienyl)cyclobutanecarboxylic Acid

The title compound was prepared in an analogous manner to that in Example 9 from 2-thienylacetonitrile and 1,3

-dibromopropane. 1-(2-Thienyl)cyclobutanecarbonitrile was chromatographed on silica gel using petroleumether-EtOAc 98:2 as eluent. The yield was 36%; $^1$H NMR (CDCl$_3$) δ 2.18 (m, 1H), 2.28 (m, 1H), 2.60 (m, 2H), 2.83 (m, 2H), 6.97 (m, 1H), 7.09 (m, 1H), 7.26 (m, 1H).

EXAMPLE 26

Starting Material 1-(3-Thienyl)cyclobutanecarboxylic Acid

The title compound was prepared in an analogous manner to that in Example 9 from 3-thienylacetonitrile and 1,3-dibromopropane. 1-(3-Thienyl)cyclobutanecarbonitrile was chromatographed on silica gel using petroleumether-EtOAc 96:4 as eluent). The yield was 60%; $^1$H NMR (CDCl$_3$) δ 2.11 (m, 1H), 2.34 (m, 1H), 2.58 (m, 2H), 2.79 (m, 2H), 7.14 (m, 1H), 7.26 (m, 1H), 7.36 (m, 1H).

EXAMPLE 27

Starting Material

1-Phenyl-3,3-diethylcyclobutanecarboxylic Acid

NaH (60% dispersion in mineral oil, 107 mmol) was washed several times with n-pentane and suspended in DMF. A mixture of 1-phenylacetonitrile (42.7 mmol) and di-O-p-toluene-sulfonyl-2-diethyl-1,3-propanediol (42.7 mmol) in DMF was added dropwise. The reaction mixture was stirred at 70° C. overnight. Excess hydride was then decomposed by the cautious addition of H$_2$O. Extraction with EtOAc, drying of the organic layer (MgSO$_4$) and evaporation of the solvent afforded 1-phenyl-3,3-diethylcyclobutanecarbonitrile (39.8 mmol) that was refluxed with KOH (40%, 490 mL) in ethyleneglycol (370 mL) for 10 h. The mixture was then allowed to cool to room temperature and was washed with EtOAc. The aqueous layer was acidified and extracted with EtOAc. The organic layer was dried (MgSO$_4$) and concentrated to provide the desired product. An oil was afforded that crystallised after treatment with MeOH:H$_2$O 1:1. The yield was 1.4 g (14%); $^1$H NMR (CDCl$_3$) δ 0.65 (t, 3H), 0.77 (t, 3H), 1.28 (q, 2H), 1.49 (q, 2H), 2.29 (d, 2H), 2.69 (d, 2H), 7.20–7.35 (m, 5H).

EXAMPLE 28

Starting Material

1-Phenyl-3,3-trimethylenecyclobutanecarboxylic Acid

The title compound was prepared in an analogous manner to that in Example 27 from 1-phenylacetonitrile and de-O-p-toluene-sulfonyl-2,2-trimethylene-1,3-propanediol. The resulting 1-phenyl-3,3-trimethyleneacetonitrile was chromatographed on silica gel using petroleumether-EtOAc 98:2 as eluent. The yield of the desired carboxylic acid was 32%; $^1$H NMR (CDCl$_3$) δ 1.93 (m, 4H), 2.36 (m, 2H), 2.60 (m, 2H), 2.89 (m, 2H), 7.38 (m, 5H).

EXAMPLE 29

Starting Material 1-Phenyl-3,3-dimethylcyclobutanecarboxylic Acid

NaH (60% dispersion in mineral oil, 77.8 mmol) was washed several times with n-pentane and suspended in DMF. Phenylacetonitrile (31 mmol) in DMF was added followed by 3-bromo-O-p-toluenesulfonyl-2,2-dimethyl-1-propanol (31 mmol) in DMF. The reaction mixture was stirred at 75° C. overnight. Excess hydride was then decomposed by the cautious addition of H$_2$O. Extraction with toluene, drying of the organic layer (MgSO$_4$) and evaporation of the solvent afforded 1-phenyl-3-dimethylcyclobutanecarbonitrile (31 mmol) that was refluxed with KOH (128 mmol) in ethyleneglycol (35 mL) for 2 h. It was then allowed to cool to room temperature, toluene and H$_2$O were added and the layers were separated. The aqueous layer was acidified and extracted with EtOAc. The organic layer was dried (MgSO$_4$) and concentrated to provide the desired product. The yield was 6.3 g (99%); $^1$H NMR (CDCl$_3$) δ 0.99 (s, 3H), 1.16 (s, 3H), 2.37 (d, 2H), 2.76 (d, 2H), 7.20–7.35 (m, 5H).

EXAMPLE 30

Starting Material

1-Phenyl-3-trans-methylcyclobutanecarboxylic Acid

The title compound was prepared in an analogous manner to that in Example 29. NaH (60% dispersion in mineral oil, 77.8 mmol) was reacted at room temperature with phenylacetonitrile and (R)-3-bromo-O-p-toluenesulfonyl-2-methyl-1-propanol that was prepared by reacting (R)-(–)-3-bromo-2-methyl-1-propanol (33 mmol) with p-toluenesulfonyl chloride (39 mmol) in pyridine for 17 h. The afforded 1-phenyl-3-methylcyclobutanecarbonitrile contained 75% of the cis isomer and 25% of the trans isomer. In order to separate the two isomers, the allylester of the acid was prepared. 1-Phenyl-3-methylcyclobutanecarboxylic acid (24 mmol) was refluxed with neat SOCl$_2$ (25 mL) for 1 h. SOCl$_2$ was then evaporated, the residue was dissolved in toluene and allylalcohol (26 mmol) and pyridine (26 mmol) were added. The mixture was stirred overnight to give allyl 1-phenyl-3-methylcyclobutanecarboxylate that was chromatographed on silica gel containing 2% AgNO$_3$ using a gradient of hexane up to hexane-EtOAc 95:5 as eluent. 1.3 g of allyl 1-phenyl-3-trans-methylcyclobutanecarboxylate was obtained. The allyl ester was then hydrolysed with KOH as described above. The obtained product contained 10% of the cis isomer. The total yield was 0.66 g (11%); $^1$H NMR (CDCl$_3$) δ 1.09 (d, 3H), 2.15–2.30 (m, 1H), 2.38–2.48 (m, 2H), 2.65–2.75 (m, 2H), 7.21–7.41 (m, 5H).

EXAMPLE 31

Starting Material

1-Phenyl-3-cis-methylcyclobutanecarboxylic Acid

The fractions containing allyl 1-phenyl-3-cis-methylcyclobutane-carboxylate afforded in preparation of 1-phenyl-3-trans-methylcyclobutanecarboxylic acid in Example 30 above were pooled and further chromatographed on silica gel using a gradient of petroleumether up to petroleumether-toluene 60:40 as eluent. Hydrolysis of the allyl ester gave the desired product that contained less than 2% of the trans isomer. The total yield was 0.18 g (1%); $^1$H NMR (CDCl$_3$) δ 1.03 (d, 3H), 2.02–2.10 (m, 2H), 2.43–2.60 (m, 1H), 2.97–3.05 (m, 2H), 7.21–7.33 (m, 5H).

EXAMPLE 32

Starting Material 1-(4-Nitrophenyl)cyclobutanecarboxylic Acid

NaH (80% dispersion in mineral oil, 0.26 mol) was suspended in DMF under nitrogen atmosphere. Methyl 4-nitrophenylacetate (0.13 mol), that was prepared by refluxing 4-nitrophenylacetic acid (0.2 mol) with MeOH (100 mL) and conc. $H_2SO_4$ (1 mL) for 24 h, dissolved in DMF was added dropwise followed by 1,3-dibromopropane (0.13 mol) in DMF. stirring was continued at room temperature for 1.5 h. Excess hydride was then decomposed by the cautious addion of $H_2O$. More $H_2O$ was added and extracted with toluene. The organic layer was washed with $H_2O$, dried ($MgSO_4$) and concentrated to give methyl 1-(4-nitrophenyl)-cyclobutanecarboxylate that was stirred with 0.5 M NaOH (128 mL) in THF overnight. THF was evaporated, the residue was dissolved in $H_2O$ and extracted with EtOAc. The aqueous layer was acidified and extracted with EtOAc. The organic layer was dried ($MgSO_4$) and concentrated to give the desired product that was washed with $EtOH/H_2O$. The yield was 0.7 g (12%); $^1H$ NMR ($CDCl_3$) δ 1.90 (m, 1H), 2.05–2.20 (m, 1H), 2.50–2.60 (m, 2H), 2.90 (m, 2H), 7.52 (d, 2H), 8.2 (d, 2H).

EXAMPLE 33

Starting Material 1-(3-Nitrophenyl)cyclobutanecarboxylic Acid

The title compound was prepared in an analogous manner to that in Example 32 from methyl 3-nitrophenylcarboxylate and 1,3-dibromopropane. 2.5 eq of NaH were used. The yield was 2.4 g (37%); $^1H$ NMR ($CDCl_3$) δ 1.95 (m, 1H), 2.10–2.25 (m, 1H), 2.50–2.65 (m, 2H), 2.95 (m, 2H), 7.50 (t, 1H), 7.60 (d, 1H), 8.10–8.20 (m, 2H).

EXAMPLE 34

Starting Material

1-Phenyl-3-methylenecyclobutanecarboxylic Acid

Methyltriphenylphosphoniumbromide (41 mmol) was added to a suspension of KOtBu (41 mmol) in toluene (200 mL). After stirring at 65° C. for 45 min, 1-cyano-1-phenyl-3-oxycyclobutane (34 mmol) was added. The reaction mixture was stirred for another 5 min. The mixture was allowed to cool to room temperature and was then washed twice with $H_2O$. The organic layer was dried ($Na_2SO_4$) and evaporated. The residue was chromatographed on silica gel using petroleumether-EtOAc 97:3 as eluent; $^1H$ NMR ($CDCl_3$) δ 3.29 (m, 2H), 3.59 (m, 2H), 5.04 (m, 2H), 7.24–7.52 (m, 5H).

The resulting 1-phenyl-3-methylenecyclobutaneacetonitrile was hydrolysed in a similar way as in Example 9. The yield of the desired carboxylic acid was 3.1 g (48%).

EXAMPLE 35

Starting Material 1-(2,4-dinitrophenyl)cyclobutanecarboxylic Acid

1-Phenylcyclobutanecarboxylic acid (28.4 mmol) was added to fuming $HNO_3$ (81 mL) kept at 0° C. and stirred for 1 h. The reaction mixture was then poured over ice and the resulting crystals were filtered off and washed with EtOH to give 5.5 g (73%) of 1-(2,4-dinitrophenyl)-cyclobutanecarboxylic acid; $^1H$ NMR ($CDCl_3$) δ 1.83–1.96 (m, 1H), 2.38–2.48 (m, 3H), 2.90–3.00 (m, 2H), 7.70 (d, 1H), 8.47 (dd, 1H), 8.77 (d, 1H).

EXAMPLE 36

2-(Diethylamino)ethyl 1-phenylcyclobutanecarboxylate Hydrochloride

1-Phenylcyclobutanecarboxylic acid (1.9 mmol) was refluxed with $SOCl_2$ (5 mL). After 0.5 h, the reaction mixture was evaporated and the residue dissolved in toluene. Diisopropylaminoethanol (3.8 mmol) was added and the mixture was heated at 80° C. for 1.5 h. The reaction mixture was filtered and chromatographed on silica gel using toluene-$Et_3N$ 95:5 as eluent. The yield was 1.3 g (73%); mp 137–139° C.; $^1H$ NMR ($D_2O$) δ 1.25 (t, 6H), 1.92–2.01 (m, 1H), 2.07–2.16 (m, 1H), 2.64 (m, 2H), 2.89 (m, 2H), 3.11 (q, 4H), 3.50 (t, 2H), 4.48 (t, 2H), 7.44 (m, 1H), 7.48 (m, 2H), 7.53 (m, 2H). Anal. ($C_{17}H_{25}NO_2 \cdot HCl$) C, H, N.

EXAMPLE 37

3-(Diethylamino)propyl 1-phenylcyclobutanecarboxylate Hydrochloride

The title compound was prepared in an analogous manner to that in Example 36 by reacting 1-phenylcyclobutanecarbonyl chloride with 3-diethylaminopropanol at 80° C. for 5 h. The reaction mixture was filtered and chromatographed on silica gel using toluene-$Et_3N$ 95:5 as eluent. The yield was 0.8 g (45%); mp 108–111° C.; $^1H$ NMR ($D_2O$) δ 1.25 (t, 6H), 1.91–2.14 (m, 4H), 2.62 (m, 2H), 2.89 (m, 4H), 3.13 (q, 4H), 4.27 (t, 2H), 7.43 (m, 1H), 7.48 (m, 2H), 7.53 (m, 2H). Anal. ($C_{18}H_{27}NO_2 \cdot HCl$) C, H, N.

EXAMPLE 38

2-(Diethylamino)ethyl 1-phenyl-3,3-dimethylcyclobutanecarboxylate Hydrochloride

The title compound was prepared in an analogous manner to that in Example 36 from the compound prepared in Example 29 and 2-diethylaminoethanol. The crude was chromatographed on silica gel using toluene-$Et_3N$ 90:10 as eluent. The yield was 0.18 g (44%); mp 185–186° C.; $^1H$ NMR ($CD_3OD$) δ 1.0 (s, 3H), 1.13–1.20 (m, 9H), 2.42 (d, 2H), 2.75 (d, 2H), 2.98 (q, 4H), 3.35 (m, 2H), 4.36 (m, 2H), 7.21–7.39 (m, 5H). Anal. ($C_{19}H_{29}NO_2 \cdot HCl \cdot 0.5H_2O$) C, N; H: calcd, 9.0; found, 8.4.

EXAMPLE 39

2-(Diethylamino)ethyl 1-phenyl-3,3-diethylcyclobutanecarboxylate Hydrochloride

The title compound was prepared in an analogous manner to that in Example 36 from the compound prepared in Example 27 and 2-diethylaminoethanol. The crude was chromatographed on silica gel using toluene-$Et_3N$ 90:10 as eluent. The yield 0.26 g (47%); mp 152–154° C.; $^1H$ NMR ($CD_3OD$) δ 0.69 (t, 3H), 0.80 (t, 3H), 1.15 (t, 6H), 1.31 (q, 2H), 1.50 (q, 2H), 2.35 (d, 2H), 2.70 (d, 2H), 2.98 (q, 4H), 3.35 (m, 2H), 4.35 (m, 2H), 7.20–7.40 (m, 5H). Anal. ($C_{21}H_{33}NO_2 \cdot HCl$) C, H, N.

EXAMPLE 40

2-(Diisopropylamino)ethyl 1-phenylcyclobutanecarboxylate Hydrochloride

The title compound was prepared in an analogous manner to that in Example 36 by reacting 1-phenylcyclobutanecarbonyl chloride with 2-diisopropylaminoethanol at 80° C. for 17 h. The undissolved oil was separated from the reaction mixture and the toluene solution was chromatographed on silica gel using toluene-$Et_3N$ 98:2 as eluent. The yield was 1.5 g (77%); mp 110–114° C.; $^1H$ NMR ($D_2O$) δ 1.33 (d, 12H), 1.97 (m, 1H), 2.11 (m, 1H), 2.63 (m, 2H), 2.89 (m, 2H), 3.47 (t, 2H), 3.70 (m, 2H), 4.46 (t, 2H), 7.44 (m, 1H), 7.48 (m, 2H), 7.53 (m, 2H). Anal. ($C_{19}H_{29}NO_2$ HCl) C, H, N.

EXAMPLE 41

2-(Diisopropylamino)ethyl 1-phenyl-2-cis-methylcyclobutanecarboxylate Hydrochloride

The title compound was prepared in an analogous manner to that in Example 36 from the compound prepared in Example 12 and 2-diisopropylaminoethanol. The crude was chromatographed on silica gel using toluene-EtOAc 90:10 as eluent. The yield was 0.16 g (32%); mp 64–66° C.; $^1$H NMR (CD$_3$OD) δ 1.15–1.25 (br, 12H), 1.27 (d, 3H), 1.81 (m, 1H), 2.08 (m, 1H), 2.18 (m, 1H), 2.93 (m, 1H), 3.09 (m, 1H), 3.35 (m, 2H), 3.49 (br, 1H), 3.57 (br, 1H), 4.33 (m, 1H), 4.52 (m, 1H), 7,24 (m, 3H), 7.34 (m, 2H).

EXAMPLE 42

2-(Diisopropylamino)ethyl 1-phenyl-2-trans-methylcyclobutanecarboxylate Hydrochloride

The title compound was prepared in an analogous manner to that in Example 36 from the compound prepared in Example 13 and 2-diisopropylaminoethanol. The crude was chromatographed on silica gel using toluene-EtOAc 90:10 as eluent. The yield was 0.30 g (60%); mp 108–112° C.; $^1$H NMR (CD$_3$OD) δ 0.72 (d, 3H), 1.25 (d, 12H), 1.50 (m, 1H), 2.19 (m, 1H), 2.56 (m, 1H), 2.80 (m, 1H), 3.20 (q, 1H), 3.32-3.45 (m, 2H), 3.60 (m, 2H), 4.41 (m, 2H), 7.27 (m, 3H), 7.37 (m, 2H). Anal. (C$_{20}$H$_{31}$NO$_2$.HCl) C, H, N.

EXAMPLE 43

2-(Diisopropylamino)ethyl 1-phenyl-3-cis-methylcyclobutanecarboxylate Hydrochloride

The title compound was prepared in an analogous manner to that in Example 36 from the compound prepared in Example 31. The crude was chromatographed using hexane-Et$_3$N 90:10 as eluent. The yield was 0.9 g (73%); mp 155–156° C.; $^1$H NMR (CD$_3$OD) δ 1.09 (d, 3H), 1.25 (d, 12H), 2.18–2.35 (m, 1H), 2.40–2.48 (m, 2H), 2.67–2.75 (m, 2H), 3.36 (t, 2H), 3.60 (t, 2H), 4.32 (t, 2H), 7.20–7.44 (m, 5H). Anal. (C$_{20}$H$_{31}$NO$_2$.HCl) C, H, N.

EXAMPLE 44

2-(Diisopropylamino)ethyl 1-phenyl-3-trans-methylcyclobutanecarboxylate Hydrochloride

The title compound was prepared in an analogous manner to that in Example 36 from the compound prepared in Example 30. The crude was chromatographed on silica gel using hexane-Et$_3$N 90:10 as eluent. The yield was 0.14 g (49%); mp 132–135° C.; $^1$H NMR (CD$_3$OD) δ 1.05 (d, 3H), 1.33 (d, 6H), 1.38 (d, 6H), 2.06–2.11 (m, 2H), 2.5 (m, 1H), 2.99–3.08 (m, 4H), 3.5 (m, 2H), 4.7 (t, 2H), 7.19–7.23 (m, 2H), 7.29–7.32 (m, 2H). Anal. (C$_{20}$H$_{31}$NO$_2$.HCl) C, H, N.

EXAMPLE 45

2-(Diisopropylamino)ethyl 1-phenyl-3,3-dimethylcyclobutanecarboxylate Hydrochloride

The title compound was prepared in an analogous manner to that in Example 36 from the compound prepared in Example 29 and 2-diisopropylaminoethanol. The crude was chromatographed using toluene-EtOAc 90:10 as eluent. The yield was 0.6 g (17%); mp 129–130° C.; $^1$H NMR (CD$_3$OD) δ 0.99 (s, 3H), 1.16 (s, 3H), 1.25 (d, 12H), 2.42 (d, 2H), 2.79 (d, 2H), 3.36 (t, 2H), 3.61 (m, 2H), 4.35.(t, 2H), 7.20–7.40 (m, 5H). Anal. (C$_{21}$H$_{33}$NO$_2$.HCl) C, H, N.

EXAMPLE 46

2-(Diisopropylamino)ethyl 1-phenyl-3,3-diethylcyclobutanecarboxylate Hydrochloride

The title compound was prepared in an analogous manner to that in Example 36 from the compound prepared in Example 27 and 2-diisopropylaminoethanol. The crude was chromatographed using hexane-Et$_3$N 90:10 as eluent. The yield was 0.38 g (45%) of a colourless oil; $^1$H NMR (CD$_3$OD) 3 0.70 (t, 3H), 0.80 (t, 3H), 1.22–1.38 (m, 14H), 1.50 (q, 2H), 2.35 (d, 2H), 2.70 (d, 2H), 3.35 (t, 2H), 3.60 (m, 2H), 4.35 (t, 2H), 7.20–7.40 (m, 5H). Anal. (C$_{23}$H$_{37}$NO$_2$.HCl) C, H, N.

EXAMPLE 47

2-(Diisopropylamino)ethyl 1-phenyl-3,3-trimethylenecyclobutanecarboxylate Fumaric Acid

The title compound was prepared in an analogous manner to that in Example 36 from the compound prepared in Example 28 and 2-diisopropylaminoethanol. The crude was chromatographed on silica gel using toluene-Et$_3$N 92:8 as eluent. Fumaric acid (1 eq) was added to the pure amine. The mixture was evaporated and the oil was dried over P$_2$O$_5$ under vacuum (1 mm Hg) for two days whereby the product crystallized to yield 0.75 g (35%); mp 126–129° C.; $^1$H NMR (CDCl$_3$) δ 1.21 (d, 12H), 1.83 (m, 4H), 2.05 (m, 2H), 2.52 (d, 2H) 2.90 (d, 2H), 3.06 (m, 2H), 3.45 (m, 2H), 4.40 (m, 2H), 6.75 (s, 2H) 7.27 (m, 5H). Anal. (C$_{22}$H$_{33}$NO$_2$.C$_4$H$_4$O$_4$.0.5H$_2$O) C, H, N.

EXAMPLE 48

2-(Diisopropylamino)ethyl 1-phenyl-3-methylenecyclobutanecarboxylate Hydrochloride

The title compound was prepared in an analogous manner to that in Example 36 from the compound prepared in Example 34 and 2-diisopropylaminoethanol. The crude was chromatographed on silica gel using toluene-Et$_3$N 97:3 as eluent. The yield was 0.62 g (55%); mp 163–164° C.; $^1$H NMR (CDCl$_3$) δ 1.36 (m, 12H), 3.19 (m, 4H), 3.53 (m, 4H), 4.70 (t, 2H), 4.87 (m, 2H), 7.32 (m, 5H), 11.7 (br, 1H). Anal. (C$_{20}$H$_{29}$NO$_2$.HCl) C, H, N.

EXAMPLE 49

2-(Diisopropylamino)ethyl 1-(3-nitrophenyl)cyclobutanecarboxylate Hydrochloride

The title compound was prepared in an analogous manner to that in Example 36 from the compound prepared in Example 33 and 2-diisopropylaminoethanol. The crude was chromatographed on silica gel using toluene-EtOAc 90:10 as eluent. The yield was 0.5 g (29%); mp 124–129° C.; $^1$H NMR (CD$_3$OD) δ 1.35 (d, 12H), 1.83–2.02 (m, 1H), 2.08–2.25 (m, 1H), 2.55–2.65 (m, 2H), 2.90–3.0 (m, 2H), 3.41 (t, 2H), 3.65 (m, 2H), 4.39 (t, 2H), 7.58–7.74 (m, 2H), 8.15 (m, 2H). Anal. (C$_{19}$H$_{28}$N$_2$O$_4$.HCl) C, H, N.

EXAMPLE 50

2-(Diisopropylamino)ethyl 1-(4-nitrophenyl)cyclobutanecarboxylate Hydrochloride

The title compound was prepared in an analogous manner to that in Example 36 from the compound prepared in Example 32 and 2-diisopropylaminoethanol. The crude was chromatographed twice on silica gel using hexane-Et$_3$N 90:10 and toluene-EtOAc 90:10 as eluent. The yield was 0.26 g (51%); mp 145–146° C.; $^1$H NMR (CD$_3$OD) δ 1.29 (d, 12H), 1.90–1.98 (m, 1H), 2.21–2.30 (m, 1H), 2.57–2.63 (m, 2H), 2.92–2.98 (m, 2H), 3.40 (t, 2H), 3.65 (m, 2H), 4.40 (t, 2H), 7.55–7.58 (m, 2H), 8.22–8.24 (m, 2H). Anal. (C$_{19}$H$_{28}$N$_2$O$_4$.HCl) C, H, N.

EXAMPLE 51

2-(Diisopropylamino)ethyl 1-(2,4-dinitrophenyl) cyclobutanecarboxylate Hydrochloride The title compound was prepared in an analogous manner to that in Example 36 from the compound prepared in Example 35 and 2-diisopropylaminoethanol. The crude was chromatographed on silica gel using toluene-EtOAc 90:10 as eluent. The yield was 0.15 g (39%); mp 134–136° C.; $^1$H NMR (CD$_3$OD) δ 1.27 (d, 12H), 1.88–1.97 (m, 1H), 2.32–2.42 (m, 1H), 2.55–2.62 (m, 2H), 2.83–2.88 (m, 2H), 3.37 (t, 2H), 3.67 (m, 2H), 4.47 (t, 2H), 7.90 (d, 1H), 8.55 (dd, 1H), 8.76 (d, 1H). Anal. (C$_{19}$H$_{27}$N$_3$O$_6$.HCl) C, H, N.

EXAMPLE 52

2-(Diisopropylamino)ethyl 1-(3,4-methylenedioxyphenyl)cyclobutanecarboxylate Hydrochloride The title compound was prepared in an analogous manner to that in Example 36 from the compound prepared in Example 11 and 2-diisopropylaminoethanol. The amine salt was recrystallized from acetone-ether. The yield was 0.16 g (32%); mp 166–167° C.; $^1$H NMR (CD$_3$OD) δ 1.30 (d, 12H), 1.91 (m, 1H), 2.04 (m, 1H), 2.48 (m, 2H), 2.82 (m, 2H), 3.39 (t, 2H), 3.65 (m, 2H), 4.39 (t, 2H), 5.93 (s, 2H), 6.81 (s, 3H). Anal. (C$_{20}$H$_{29}$NO$_4$.HCl) C, H, N.

EXAMPLE 53

2-(Diisopropylamino)ethyl 1-(2,3-benzophenyl) cyclobutanecarboxylate Hydrochloride The title compound was prepared in an analogous manner to that in Example 36 from the compound prepared in Example 14 and 2-diisopropylaminoethanol. The HCl-salt was recrystallized twice from acetone to give 2.85 g (34%); mp 199–201° C.; $^1$H NMR (CD$_3$OD) δ 1.00 (m, 12H), 1.98 (m, 1H), 2.28 (m, 1H), 2.75 (m, 2H), 3.08 (m, 2H), 3.28 (m, 4H), 4.32 (t, 2H), 7.40–8.00 (m, 7H). Anal. (C$_{23}$H$_{31}$NO$_2$.HCl) C, H, N.

EXAMPLE 54

2-(Diisopropylamino)ethyl 1-(3,4-benzophenyl) cyclobutanecarboxylate Hydrochloride The title compound was prepared in an analogous manner to that in Example 36 from the compound prepared in Example 15 and 2-diisopropylaminoethanol. The yield was 1.98 g (73 %); mp 129–132° C.; $^1$H NMR (CD$_3$OD) δ 1.11 (d, 12H), 1.95 (m, 1H), 2.11 (m, 1H), 2.67 (m, 2H), 2.94 (m, 2H), 3.33 (t, 2H), 3.47 (m, 2H), 4.38 (t, 2H), 7.38 (d, 1H), 7.50 (m, 2H), 7.84 (m, 4H). Anal. (C$_{23}$H$_{31}$NO$_2$.HCl) C, H, N.

EXAMPLE 55

2-(Diisopropylamino)ethyl 1-(3-thienyl) cyclobutanecarboxylate Hydrochloride

The title compound was prepared in an analogous manner to that in Example 36 from the compound prepared in Example 26. The crude was chromatographed on silica gel using toluene-Et$_3$N 98:2. The yield was 0.28 g (18%); mp 125–126 ° C. $^1$H NMR (CDCl$_3$) δ 1.40 (m, 12H), 1.95 (m, 2H), 2.43 (m, 2H), 2.81 (m, 2H), 3.10 (m, 2H), 3.56 (m, 2H), 4.72 (m, 2H), 7.02 (dd, 1H), 7.15 (dd, 1H), 7.29 (dd, 1H). Anal. (C$_{17}$H$_{27}$NO$_2$S.HCl) C, H, N.

EXAMPLE 56

2-(1-Pyrrolidino)ethyl 1-phenylcyclobutanecarboxylate Hydrochloride

The title compound was prepared in an analogous manner to that in Example 36 by reacting 1-phenylcyclobutanecarbonyl chloride with 1-(2-hydroxyethyl)pyrrolidine at 80° C. for 21 h. The yield was 0.9 g (50%); mp 150–153° C.; $^1$H NMR (DMSO-d$_6$, 1% TFA) δ 1.73–1.90 (m, 5H), 1.98 (m, 1H), 2.47 (m, 2H), 2.72–2.82 (m, 4H), 3.26 (m, 2H), 3.37 (m, 2H), 4.35 (t, 2H), 7.24 (t, 1H), 7.30 (d, 2H), 7.35 (t, 2H). Anal. (C$_{17}$H$_{23}$NO$_2$.HCl) C, H, N.

EXAMPLE 57

(1-Methyl-2-piperidino)methyl 1-phenylcyclobutanecarboxylate Hydrochloride

The title compound was prepared in an analogous manner to that in Example 36 by reacting 1-phenylcyclobutanecarbonyl chloride with 1-methyl-2-piperidinemethanol at 80° C. for 17 h. The yield was 1.1 g (61%); mp 159–162° C.; $^1$H NMR (DMSO-d$_6$, 1% TFA) δ 1.42 (m, 1H), 1.54 (m, 1H), 1.60–1.87 (m, 5H), 1.97 (m, 1H), 2.42–2.55 (m, 5H), 2.81 (m, 2H), 2.95 (m, 0.8H), 3.11 (m, 0.4H), 3.21–3.35 (m, 1.6H), 3.53 (m, 0.2H), 4.21–4.39 (m, 2H), 7.26 (m, 1H), 7.31–7.38 (m, 4H). Anal. (C$_{18}$H$_{25}$NO$_2$.HCl) H, N; C: calcd, 66.8; found, 67.5. The compound exists in two forms in DMSO-TFA solution.

EXAMPLE 58

(1-Methyl-3-piperidino)methyl 1-phenylcyclobutanecarboxylate Hydrochloride

The title compound was prepared in an analogous manner to that in Example 36 by reacting 1-phenylcyclobutanecarbonyl chloride with 1-methyl-3-piperidinemethanol at 80° C. for 18 h. The yield was 1.4 g (77%); mp 126–128° C.; $^1$H NMR (D$_2$O) δ 1.15 (m, 1H), 1.67–1.81 (m, 2H), 1.97 (m, 2H), 2.05–2.19 (m, 2H), 2.42 (t, 1H), 2.64 (m, 2H), 2.73 (m, 1H), 2.80 (s, 3H), 2.87 (m, 2H), 3.17 (d, 1H), 3.49 (d, 1H), 4.09 (q, 1H), 4.17 (q, 1H), 7.44 (t, 1H), 7.49 (d, 2H), 7.54 (t, 2H). Anal. (C$_{18}$H$_{25}$NO$_2$.HCl) C, H, N.

EXAMPLE 59

(1-Methyl-3-piperidino)methyl 1-phenyl-3,3-dimethylcyclobutanecarboxylate Hydrochloride The title compound was prepared in an analogous manner to that in Example 36 from the compound prepared in Example 29 and 1-methyl-3-piperidinemethanol. The crude was chromatographed on silica gel using EtOAc-Et$_3$N 90:10 as eluent. The yield was 0.54 g (42%); mp 155–157° C.; $^1$H NMR (CD$_3$OD) δ 1.0–1.15 (m, 7H), 1.62–1.90 (m, 3H), 2.03 (br, 1H), 2.3–2.41 (m, 3H), 2.6–2.8 (m, 6H), 3.0 (brd, 1H), 3.3–3.4 (m, 1H), 4.0 (m, 2H), 7.22–7.40 (m, 5H). Anal. (C$_{20}$H$_{29}$NO$_2$.HCl.0.4H$_2$O) C, H, N.

EXAMPLE 60

1-Methyl-4-piperidinyl 1-phenylcyclobutanecarboxylate Hydrochloride

The title compound was prepared in an analogous manner to that in Example 36 by reacting 1-phenylcyclobutanecarbonyl chloride with 1-methyl-4-hydroxypiperidine at 80° C. for 20 h. The yield was 0.77 g (44%); mp 203–206° C.; $^1$H NMR (DMSO-d$_6$, 1% TFA) δ 1.76 (d, 2H), 1.83 (m, 1H), 1.96 (m, 2H), 2.05 (t, 1H), 2.41–2.51 (m, 2H), 2.53–2.85 (m, 6H), 3.03 (q, 1H), 3.20 (d, 1H), 3.34 (d, 1H), 4.8 (m, 0.4H), 4.93 (m, 0.6H), 7.23–7.40 (m, 5H). Anal. (C$_{17}$H$_{23}$NO$_2$.HCl) C, H. N. The compound exists in two forms in DMSO-TFA solution.

EXAMPLE 61

1-Methyl-4-piperidinyl 1-phenyl-3,3-dimethylcyclobutanecarboxylate Hydrochloride The title compound was prepared in an analogous manner to that in Example 36 from the compound prepared in Example 29 and 1-methyl-4-hydroxypiperidine. The crude was chromatographed on silica gel using EtOAc-Et$_3$N 90:10 as eluent. The yield was 0.56 g (45%); mp 204–205° C.; $^1$H NMR (DMSO-d$_6$) δ 0.98 (s, 3H), 1.11 (s, 3H), 1.73 (br, 2H), 1.97 (br, 2H), 2.30–2.35 (m, 2H), 2.63 (s, 3H), 2.66–2.71 (m, 2H), 3.09 (br, 2H), 3.35 (br, 2H), 4.83 (br, 1H), 7.22–7.39 (m, 5H). Anal. (C$_{19}$H$_{27}$NO$_2$.HCl) C, H, N.

EXAMPLE 62

1-Methyl-3-pyrrolidinyl 1-phenylcyclobutanecarboxylate Hydrochloride

The title compound was prepared in an analogous manner to that in Example 36 by reacting 1-phenylcyclobutanecarbonyl chloride with 1-methyl-3-hydroxypyrrolidine at 80° C. for 17 h. The yield was 1.1 g (67%); mp 153–155° C.; $^1$H NMR (DMSO-d$_6$, 1% TFA) δ 1.83 (m, 1.5H), 1.96 (m, 1.5H), 2.17 (m, 0.5H), 2.38–2.51 (m, 2.5H), 2.64 (t, 1.5H), 2.73–2.92 (m, 4H), 2.97 (m, 0.5H), 3.06 (m, 0.5H), 3.32 (m, 0.5H), 3.54 (m, 1.5H), 3.76 (m, 0.5H), 5.26 (m, 1H), 7.23–7.39 (m, 5H). Anal. (C$_{16}$H$_{21}$NO$_2$.HCl) C, H, N. The compound exists in two forms in DMSO-TFA solution.

EXAMPLE 63

3-Tropanyl 1-phenylcyclobutanecarboxylate hydrochloride

The title compound was prepared in an analogous manner to that in Example 36 by reacting 1-phenylcyclobutanecarbonyl chloride with tropine at 80° C. for 22 h. The yield was 0.5 g (28%); mp 181–183° C.; $^1$H NMR (D$_2$O) δ 1.78 (q, 2H), 1.96 (m, 1H), 2.04 (d, 2H), 2.13 (m, 3H), 2.38 (m, 2H), 2.64 (m, 2H), 2.77 (s, 3H), 2.87 (m, 2H), 3.82 (m, 2H), 5.07 (t, 1H), 7.42 (m, 1H), 7.47 (m, 2H), 7.52 (m, 2H). Anal. (C$_{19}$H$_{25}$NO$_2$.HCl) C, H, N.

EXAMPLE 64

3-Quinuclidinyl 1-phenylcyclobutanecarboxylate Hydrochloride

The title compound was prepared in an analogous manner to that in Example 36 by reacting 1-phenylcyclobutancarbonyl chloride with 3-quinuclidinol at 80° C. for 15 h. The yield was 0.4 g (22%); mp 163–168° C.; $^1$H NMR (D$_2$O) δ 1.80 (m, 2H), 1.88–2.02 (m, 2H), 2.04–2.17 (m, 2H), 2.38 (m, 1H), 2.59–2.70 (m, 2H), 2.90 (m, 2H), 3.08 (q, 1H), 3.18 (d, 1H), 3.28–3.39 (m, 3H), 3.69 (m, 1H), 5.18 (m, 1H), 7.42 (m, 1H), 7.47–7.54 (m, 4H). Anal. (C$_{18}$H$_{23}$NO$_2$.HCl.0.5H$_2$O) C, H, N.

EXAMPLE 65

3-(R)-Quinuclidinyl 1-phenylcyclobutanecarboxylate Hydrochloride

The title compound was prepared in an analogous manner to that in Example 36 by reacting 1-phenylcyclobutanecarbonyl chloride with R(−)-3-quinuclidinol at 80° C. for 30 h. The yield was 0.43 g (31%); mp 219–223° C.; $^1$H NMR (D$_2$O) δ 1.80 (m, 2H), 1.88–2.02 (m, 2H), 2.04–2.17 (m, 2H), 2.38 (m, 1H), 2.59–2.70 (m, 2H), 2.90 (m, 2H), 3.08 (q, 1H), 3.18 (d, 1H), 3.28–3.39 (m, 3H), 3.69 (m, 1H), 5.18 (m, 1H), 7.42 (m, 1H), 7.47–7.54 (m, 4H). Anal. (C$_{18}$H$_{23}$NO$_2$.HCl) C, H, N.

EXAMPLE 66

3-Quinuclidinyl 1-phenyl-3,3-dimethylcyclobutanecarboxylate Hydrochloride

The title compound was prepared in an analogous manner to that in Example 36 from the compound prepared in Example 29 and 3-quinuclidinol. The crude was chromatographed on silica gel using EtOAc-Et$_3$N 90:10 as eluent. The yield was 0.4 g (18%); mp 215–218° C.; $^1$H NMR (CD$_3$OD) δ 1.01 (s, 3H), 1.16 (s, 3H), 1.62–1.70 (m, 2H), 1.80–2.05 (m, 2H), 2.22 (br, 1H), 2.42 (m, 2H), 2.75–2.98 (m, 4H), 3.22 (m, 3H), 3.60–3.70 (m, 1H), 5.0 (m, 1H), 7.2–7.38 (m, 5H). Anal. (C$_{20}$H$_{27}$NO$_2$.Cl) C, H, N.

EXAMPLE 67

3-(R)-Quinuclidinyl 1-phenyl-3,3-dimethylcyclobutanecarboxylate Hydrochloride

The title compound was prepared in an analogous manner to that in Example 36 from the compound prepared in Example 29 and R(−)-3-quinuclidinol. The crude was chromatographed on silica gel using EtOAc-Et$_3$N 90:10 as eluent. The yield was 0.19 g (45%); mp 212–214° C.; $^1$H NMR (CD$_3$OD) δ 1.03 (s, 3H), 1.18 (s, 3H), 1.65–2.05 (m, 4H), 2.23 (br, 1H), 2.44 (m, 2H), 2.75–3.00 (m, 4H), 3.23 (m, 3H), 3.60–3.70 (m, 1H), 5.02 (m, 1H), 7.02–7.37 (m, 5H). Anal. (C$_{20}$H$_{27}$NO$_2$.HCl) C, H, N.

EXAMPLE 68

3-Quinuclidinyl 1-(2-methylphenyl) cyclobutanecarboxylate Hydrochloride

The title compound was prepared in an analogous manner to that in Example 36 from the compound prepared in Example 19 and 3-quinuclidinol. The crude was chromatographed on silica gel using toluene-Et$_3$N 94:6 as eluent. The yield was 0.19 g (8%); mp 186–190° C.; $^1$H NMR (CDCl$_3$) δ 1.32 (m, 1H), 1.49 (m, 1H), 1.92 (m, 3H), 2.10–2.38 (m, 5H), 2.49–3.17 (m, 6H), 3.22 (m, 3H), 3.54 (m, 1H), 5.07 (m, 1H), 7.17 (m, 4H). Anal. (C$_{19}$H$_{25}$NO$_2$.HCl) C, H, N.

EXAMPLE 69

3-Quinuclidinyl 1-(3-methylphenyl) cyclobutanecarboxylate Hydrochloride

The title compound was prepared in an analogous manner to that in Example 36 from the compound prepared in Example 16 and 3-quinuclidinol. 1-(3-Methylphenyl) cyclobutanecarbonyl chloride was reacted with 3-quinuclidinol at room temperature for 15 min. The eluent was evaporated and the residue was partitioned between Et$_2$O and NaOH. The organic layer was extracted with 3 M HCl that was basidified and extracted with Et$_2$O. HCl (g)/Et$_2$O was then added whereby the product crystallized to yield 0.25 g (53%); mp 196.5–198° C.; $^1$H NMR (CDCl$_3$) δ 1.51 (m, 2H), 1.76–2.20 (m, 5H), 2.32 (s, 3H), 2.51 (m, 2H), 2.70–2.80 (m, 3H), 3.03 (d, 1H), 3.24 (m, 3H), 3.52 (m, 1H), 5.00 (m, 1H), 7.05–7.30 (m, 4H)$_1$ 12.31 (bs, 1H). Anal. (C$_{19}$H$_{25}$NO$_2$.HCl) C, H, N, Cl.

EXAMPLE 70

3-Quinuclidinyl 1-(4-methylphenyl) cyclobutanecarboxylate Hydrochloride

The title compound was prepared in an analogous manner to that in Example 36 from the compound prepared in Example 18 and 3-quinuclidinol. The yield was 0.45 g (23%); mp 209–211° C.; $^1$H NMR (CDCl$_3$) δ 1.57 (m, 2H), 1.88 (m, 4H), 2.33 (s, 3H), 2.55 (m, 2H), 2.83 (m, 5H), 3.23 (m, 3H), 3.55 (ddd, 1H), 5.02 (br, 1H), 7.14 (s, 4H). Anal. (C$_{19}$H$_{25}$NO$_2$.HCl) C, H, N.

EXAMPLE 71

3-Quinuclidinyl 1-(2-methoxyphenyl) cyclobutanecarboxylate Hydrochloride

The title compound was prepared in an analogous manner to that in Example 36. 1-(2-Methoxyphenyl) cyclobutanecarbonyl chloride, prepared from the compound prepared in Example 17, was reacted with 3-quinuclidinol at 80° C. for 25 h. A crude product was obtained which was rechromatographed on a reverse-phase PEP RPC HR 30/26 column using a gradient of 25–50% CH$_3$CN with 0.1% TFA. The yield was 0.2 g (6%); mp 121–123° C.; $^1$H NMR (D$_2$C) δ 1.70–1.85 (m, 2H), 1.93–2.03 (m, 2H), 2.10 (m, 1H), 2.19 (m, 1H), 2.39 (m, 1H), 2.54 (m, 2H), 2.77 (m, 2H), 3.01 (q, 1H), 3.18 (d, 1H), 3.28–3.37 (m, 3H), 3.75 (m, 1H), 3.85 (s, 3H), 5.24 (m, 1H), 7.13 (d, 1H), 7.17 (t, 1H), 7.45 (t, 1H), 7.53 (d, 1H). Anal. (C$_{19}$H$_{25}$NO$_2$.HCl.H$_2$O) C, H, N.

EXAMPLE 72

3-Quinuclidinyl 1-(3-methoxyphenyl) cyclobutanecarboxylate Hydrochloride

The title compound was prepared in an analogous manner to that in Example 36 from the compound prepared in Example 23 and 3-quinuclidinol. The crude was chromatographed on silica gel using CHCl$_3$-MeOH-conc. ammonia 98:2:0.2 as eluent. The yield was 0.42 g (5%) of hygroscopic crystals; mp 151–153° C.; $^1$H NMR (CDCl$_3$) δ 1.59 (m. 2H), 1.92 (m, 4H), 2.31 (m, 1H), 2.53 (m, 2H), 2.88 (m, 4H), 3.22 (m, 3H), 3.56 (m, 1H), 3.80 (s, 3H), 5.02 (m, 1H), 6.80 (m, 3H), 7.21 (m, 1H). Anal. (C$_{19}$H$_{25}$NO$_3$.HCl) C, H, N.

EXAMPLE 73

3-Quinuclidinyl 1-(4-methoxyphenyl) cyclobutanecarboxylate Hydrochloride

The title compound was prepared in an analogous manner to that in Example 36 from the compound prepared in Example 24 and 3-quinuclidinol. The crude was chromatographed on silica gel using CHCl$_3$-MeOH-conc. ammonia 98:2:0.2 as eluent. The yield was 0.16 g (9%); mp 173–179° C. $^1$H NMR (CDCl$_3$) δ 1.59 (m, 2H), 1.92 (m, 4H), 2.32 (m, 1H), 2.51 (m, 2H), 2.90 (m, 4H), 3.20 (m, 3H), 3.52 (m, 1H), 3.80 (s, 3H), 5.01 (m, 1H), 6.83 (d, 2H), 7,17 (d, 2H). Anal. (C$_{19}$H$_{25}$NO$_3$.HCl) C, H, N.

EXAMPLE 74

3-Quinuclidinyl 1-(2-fluorophenyl) cyclobutanecarboxylate Hydrochloride

The title compound was prepared in an analogous manner to that in Example 36 from the compound prepared in Example 21 and 3-quinuclidinol. The crude was chromatographed on silica gel using toluene-Et$_3$N 94:6 as eluent. The yield was 0.42 g (18%); mp 155–157° C.; $^1$H NMR (CDCl$_3$) δ 1.20–3.33 (m, 16H) 3.58 (m, 1H), 5.09 (m, 1H), 6.99–7.31 (m, 4H). Anal. (C$_{18}$H$_{22}$FNO$_2$.HCl) C, H, N.

EXAMPLE 75

3-Quinuclidinyl 1-(3-fluorophenyl) cyclobutanecarboxylate Hydrochloride

The title compound was prepared in an analogous manner to that in Example 36 from the compound prepared in Example 22 and 3-quinuclidinol. The crude was chromatographed on silica gel using toluene-Et$_3$N 94:6 as eluent. The yield was 0.54 g (25%); mp 179–184° C.; $^1$H NMR (CDCl$_3$) δ 1.61 (m, 2H), 1.99 (m, 4H), 2.36 (m, 1H), 2.53 (m, 2H), 2.93 (m, 4H), 3.24 (m, 3H), 3.58 (m, 1H), 5.04 (m, 1H), 6.98 (m, 3H), 7.37 (m, 1H). Anal. (C$_{18}$H$_{22}$FNO$_2$.HCl) C, H, N.

EXAMPLE 76

3-Quinuclidinyl 1-(4-fluorophenyl) cyclobutanecarboxylate Hydrochloride

The title compound was prepared in an analogous manner to that in Example 36 from the compound prepared in Example 20 and 3-quinuclidinol. The crude was chromatographed on silica gel using toluene-Et$_3$N 94:6 as eluent. The yield was 0.65 g (31%); mp 189–192 1C; $^1$H NMR (CDCl$_3$) δ 1.59 (m, 2H), 1.97 (m, 4H), 2.13 (m, 2H), 2.52 (m, 2H), 2,93 (m, 4H), 3.25 (m, 2H), 3.63 (m, 1H), 5.03 (m, 1H), 7.04 (m, 2H), 7.22 (m, 2H). Anal. (C$_{18}$H$_{22}$FNO$_2$.HCl) C, H, N.

EXAMPLE 77

3-Quinuclidinyl 1-(4-chlorophenyl) cyclobutanecarboxylate Hydrochloride

The title compound was prepared in an analogous manner to that in Example 36 by reacting 1-(4-chlorophenyl)-cyclobutanecarbonyl chloride with 3-quinuclidinol at 80° C. for 25 h. The yield was 0.7 g (43%); mp 205–208° C.; 1H NMR (D$_2$O) δ 1.73–1.85 (m, 2H), 1.86–1.97 (m, 2H), 2.04–2.15 (m, 2H), 2.32 (m, 1H), 2.48–2.63 (m, 2H), 2.87 (m, 2H), 3.12 (m, 1H), 3.22 (d, 1H), 3.27–3.42 (m, 3H), 3.73 (m, 1H), 5.17 (m, 1H), 7.37 (d, 2H), 7.43 (d, 2H). Anal. (C$_{18}$H$_{22}$ClNO$_2$.HCl) C, H, N.

EXAMPLE 78

3-Quinuclidinyl 1-(2-bromophenyl) cyclobutanecarboxylate Hydrochloride

The title compound was prepared in an analogous manner to that in Example 36. 1-(2-Bromophenyl) cyclobutanecarbonyl chloride, prepared from the compound prepared in Example 9, was reacted with 3-quinuclidinol at 75° C. overnight. The crude was chromatographed on silica gel using EtOAc-Et$_3$N 90:10 as eluent. The yield was 0.2 g (6%); mp 194–200° C.; $^1$H NMR (CD$_3$OD) δ 1.47–1.74 (m, 2H), 1.82–2.50 (m, 3H), 2.18–2.35 (m, 2H), 2.54–2.71 (m, 2H), 2.79–2.97 (m, 3H), 3.11–3.27 (m, 4H), 3.67–3.75 (m, 1H), 5.10 (m, 1H), 7.16–7.22 (m, 1H), 7.37–7.49 (m, 2H), 7.57 (dd, 1H). Anal. (C$_{18}$H$_{22}$BrNO$_2$.HCl) C, H, N.

EXAMPLE 79

3-Quinuclidinyl 1-(4-bromophenyl) cyclobutanecarboxylate Hydrochloride

The title compound was prepared in an analogous manner to that in Example 36. 1-(4-Bromophenyl)

cyclobutanecarbonyl chloride, prepared from the compound prepared in Example 10, was refluxed with 3-quinuclidinol overnight. The crude was chromatographed on silica gel using EtOAc-Et$_3$N 90:10 as eluent. The yield was 0.46 g (19%); mp 222–226° C.; $^1$H NMR (CD$_3$OD) δ 1.73 (m, 2H), 1.82–2.15 (m, 4H), 2.23 (br, 1H), 2.53 (m, 2H), 2.85 (m, 2H), 2.95–3.10 (m, 2H), 3.20–3.35 (m, 3H), 3.66 (m, 1H), 5.06 (m, 1H), 7.25 (d, 2H), 7.50 (d, 2H). Anal. (C$_{18}$H$_{22}$BrNO$_2$.HCl) C, H, N.

EXAMPLE 80

3-Quinuclidinyl 1-(3-nitrophenyl) cyclobutanecarboxylate Hydrochloride

The title compound was prepared in an analogous manner to that in Example 36. 1-(3-Nitrophenyl) cyclobutanecarbonyl chloride, prepared from the compound prepared in Example 33, was reacted with 3-quinuclidinol in CH$_2$Cl$_2$ for 2 h. The crude was chromatographed on silica gel using EtOAc-Et$_3$N 90:10 as eluent. The yield was 0.4 g (26%); mp 191–192° C.; $^1$H NMR (CD$_3$OD) δ 1.73–2.29 (m, 7H), 2.62 (m, 2H), 2.94 (m, 2H), 3.02–3.36 (m, 5H), 3.65–3.75 (m, 1H), 5.10 (m, 1H), 7.60–7.66 (m, 1H), 7.74–7.78 (m, 1H), 8.13–8.18 (m, 2H). Anal. (C$_{18}$H$_{22}$N$_2$O$_4$.HCl) C, H, N.

EXAMPLE 81

3-Quinuclidinyl 1-(3,4-methylenedioxyphenyl)-cyclobutanecarboxylate Hydrochloride The title compound was prepared in an analogous manner to that in Example 36 from the compound prepared in Example 11 and 3-quinuclidinol. The amine salt was recrystallized from acetone-ether. The yield was 0.23 g (15%); mp 194–195 ° C.; $^1$H NMR (CD$_3$OD) δ 1.70–2.10 (m, 6H), 2.26 (m, 1H), 2.50 (m, 2H), 2.80 (m, 2H), 3.04 (m, 2H), 3.30 (m, 3H), 3.68 (m, 1H), 5.07 (m, 1H), 5.94 (s, 2H), 6.81 (m, 3H). Anal. (C$_{19}$H$_{23}$NO$_4$.HCl) H, N; C: calcd, 62.4; found, 61.9.

EXAMPLE 82

3-Quinuclidinyl 1-(2,3-benzophenyl) cyclobutanecarboxylate Hydrochloride

The title compound was prepared in -an analogous manner to that in Example 36 from the compound prepared in Example 14 and 3-quinuclidinol. The reaction with SOCl$_2$ was performed at room temperature for 1 h. The residue was dissolved in n-hexane and 1 g oily contamination was separated. 1-(2,3-Benzophenyl)cyclobutanecarbonyl chloride was reacted with 3-quinuclidinol at 85° C. for 6 h. The crude was chromatographed on silica gel using toluene-EtOAc-Et$_3$N 70:20:10 as eluent. The HCl-salt was recrystallized twice from acetone to give 0.4 g (9%); mp 172–177° C.; $^1$H NMR (CD$_3$OD) δ 1.02 (m, 1H), 1.38 (m, 1H), 1.82 (m, 2H), 1.98 (m, 2H), 2.29 (m, 1H), 2.78 (m, 3H), 3.02 (m, 6H), 3.58 (m, 1H), 5.04 (m, 1H), 7.51 (m, 4H), 7.78 (m, 2H), 7.90 (m, 1H). Anal. (C$_{22}$H$_{25}$NO$_2$.HCl) C, H, N.

EXAMPLE 83

3-Quinuclidinyl 1-(3,4-benzophenyl) cyclobutanecarboxylate Hydrochloride

The title compound was prepared in an analogous manner to that in Example 36 from the compound prepared in Example 15 and 3-quinuclidinol. The reaction with SOCl$_2$ was performed at room temperature for 1 h. 1-(3,4-Benzophenyl)cyclobutanecarbonyl chloride was reacted with 3-quinuclidinol at 85° C. overnight. The crude was chromatographed on silica gel using toluene-EtOAc-Et$_3$N 70:20:10. The yield was 1.16 g (38%); mp 197–199° C.; $^1$H NMR (CD$_3$OD) δ 1.63 (m, 2H), 1.85 (m, 1H), 1.96 (m, 2H), 2.12 (m, 1H), 2.22 (m, 1H), 2.68 (m, 2H), 2.95 (m, 4H), 3.19 (m, 3H), 3.65 (m, 1H), 5.07 (m, 1H), 7.46 (m, 3H), 7.84 (m, 4H). Anal. (C$_{22}$H$_{25}$NO$_2$.HCl) C, H, N.

EXAMPLE 84

3-Quinuclidinyl 1-(2-thienyl)cyclobutanecarboxylate Hydrochloride

The title compound was prepared in an analogous manner to that in Example 36 from the compound prepared in Example 25 and 3-quinuclidinol. The crude was chromatographed on silica gel using toluene-Et$_3$N 94:6 as eluent. The yield was 0.71 g (22%); mp 196–197° C.; $^1$H NMR (CDCl$_3$) δ 1.60–2.15 (m, 6H), 2.38 (m, 1H), 2.57 (m, 2H), 2.81 (m, 2H), 3.03 (m, 2H), 3.28 (m, 3H), 3.62 (m, 1H), 5.07 (m, 1H), 6.95 (m, 2H), 7.24 (dd, 1H). Anal. (C$_{16}$H$_{21}$NO$_2$S.HCl) C, H, N.

EXAMPLE 85

3-Quinuclidinyl 1-(3-thienyl)cyclobutanecarboxylate Hydrochloride

The title compound was prepared in an analogous manner to that in Example 36 from the compound prepared in Example 26 and 3-quinuclidinol. The crude was chromatographed on silica gel using toluene-Et$_3$N 94:6 as eluent. The yield was 0.57 g (23%); mp 200–202° C.; $^1$H NMR (CDCl$_3$) δ 1.66 (m, 2H), 1.97 (m, 4H), 2.41 (m, 3H), 2.78 (m, 2H), 3.06 (m, 2H), 3.28 (m, 3H), 3.63 (m, 1H), 5.04 (m, 1H), 6.98 (dd, 1H), 7.14 (dd, 1H), 7.31 (dd, 1H). Anal. (C$_{16}$H$_{21}$NO$_2$S.HCl) C, H, N.

EXAMPLE 86

2-endo-Methyl-3-quinuclidinyl 1-phenylcyclobutanecarboxylate Hydrochloride

The title compound was prepared in an analogous manner to that in Example 36 by reacting 1-phenylcyclobutanecarbonyl chloride with 2-methyl-3-quinuclidinol at 80° C. for 30 h. The reaction mixture was filtered and chromatographed on silica gel using toluene-Et$_3$N 95:5 as eluent in order to separate the two afforded isomers. The endo isomer eluted earlier than the exo isomer. The yield of the endo isomer was 0.60 g (32%); mp 193–196° C.; $^1$H NMR (D$_2$O) δ 1.51 (d, 3H), 1.76–2.17 (m, 6H), 2.33 (m, 1H), 2.65 (m, 2H), 2.90 (m, 2H), 3.12 (m, 1H), 3.22 (m, 1H), 3.35–3.47 (m, 3H), 4.76 (m, 1H), 7.42 (m, 1H), 7.46–7.54 (m, 4H). Anal. (C$_{19}$H$_{25}$NO$_2$.HCl) C, H, N.

EXAMPLE 87

2-exo-Methyl-3-quinuclidinyl 1-phenylcyclobutanecarboxylate Hydrochloride

The yield of the exo isomer afforded in the synthesis in Example 86 above was 0.24 g (13%); mp 204–207° C.; $^1$H NMR (D$_2$O) δ 1.15 (d, 3H), 1.62–1.76 (m, 2H), 1.90–2.19 (m, 4H), 2.36 (m, 1H), 2.68 (m, 2H), 2.92 (m, 2H), 3.21 (m, 2H), 3.29–3.43 (m, 2H), 3.92 (m, 1H), 5.24 (m, 1H), 7.42 (m, 1H), 7.48–7.54 (m, 4H). Anal. (C$_{19}$H$_{25}$NO$_2$.HCl) C, H ,N.

EXAMPLE 88

3-endo-(1-Azabicyclo[3.3.1]nonyl) 1-phenylcyclobutanecarboxylate Hydrochloride

The title compound was prepared in an analogous manner to that in Example 36 by reacting 1-phenylcyclobutanecarbonyl chloride with 3-hydroxy-1-azabicyclo[3.3.1]nonane at 80° C. for 27 h. The reaction mixture was filtered and chromatographed on silica gel using toluene-Et$_3$N 95:5 as eluent in order to separate the two afforded isomers. The endo isomer eluted earlier than the exo isomer. The yield of the endo isomer was 0.21 g (14%); mp 223–228° C.; $^1$H NMR (D$_2$O) δ 1.83–2.01 (m, 5H), 2.09 (m, 2H), 2.21 (q, 1H), 2.40 (s, 1H), 2.62 (m, 2H), 2.87 (m, 2H), 3.27–3.37 (m, 3H), 3.40–3.51 (m, 2H), 3.64 (q, 1H), 5.64 (m, 1H), 7.42 (t, 1H), 7.44–7.53 (m, 4H). Anal. (C$_{19}$H$_{25}$NO$_2$.HCl) C, H. N.

EXAMPLE 89

3-exo-(1-Azabicyclo[3.3.1]nonyl) 1-phenylcyclobutanecarboxylate Hydrochloride The yield of the exo isomer afforded in the synthesis in Example 88 above was 0.33 g (21%); mp 167–170° C.; $^1$H NMR (D$_2$O) δ 1.50 (d, 2H), 1.70–1.82 (m, 2H), 1.98 (m, 1H), 2.13 (m, 2H), 2.24 (s, 1H), 2.37 (m, 1H), 2.65 (m, 2H), 2.88 (m, 2H), 3.10 (q, 1H), 3.20 (d, 1H), 3.26–3.38 (m, 3H), 3.83 (q, 1H), 5.30 (t, 1H), 7.42 (t, 1H), 7.47 (d, 2H), 7.52 (t, 2H). Anal. (C$_{19}$H$_{25}$NO$_2$.HCl) C, H, N.

EXAMPLE 90

3-Methylidenequinuclidinyl 1-phenylcyclobutanecarboxylate Hydrochloride

The title compound was prepared in an analogous manner to that in Example 36 by reacting 1-phenylcyclobutanecarboxylate hydrochloride with 3-methylidenequinuclidinol. The esterification was carried out in CH$_2$Cl$_2$. The crude was chromatographed on silica gel using toluene-Et$_3$N 88:12 as eluent. The yield was 0.07 g (9%); mp 155–157° C.; $^1$H NMR (CDCl$_3$) δ 1.80–2.10 (m, 7H), 2.25 (m, 1H), 2.52 (m, 2H), 2.76 (m, 3H), 3.18 (m, 5H), 4.09 (m, 2H), 7.29 (m, 5H), 12.2 (br, 1H). Anal. (C$_{19}$H$_{25}$NO$_2$.HCl) H, N; C: calcd, 67.94; found, 67.25.

EXAMPLE 91

2-(Diisopropylamino)ethyl 1-phenyl-3-oxocyclobutanecarboxylate Hydrochloride 1-Phenyl-3-oxocyclobutanecarboxylic acid was prepared by refluxing 1-phenyl-3,3-dimethoxycyclobutanecarboxylic acid (8.5 mmol) with 90% HOAc, evaporating the reaction mixture, taking up the residue in 0.1 M HCl and Et$_2$O, extracting the aqueous layer with Et$_2$O and drying (Na$_2$SO$_4$) and evaporating the organic layer. The crude oxocarboxylic acid was dissolved in DMF (30 mL) and then added to NaH (60% dispersion in mineral oil, 20 mmol, washed twice with hexane) at ambient temperature. After 30 min N,N-diisopropyl-2-chloroethylamine (1.8 mmol) was added. After 2 h, the reaction mixture was partitioned between H$_2$O and toluene. The crude product was chromatographed on silica gel using toluene-Et$_3$N 98:2 as eluent. The afforded oil was dissolved in Et$_2$O and HCl (g)/Et$_2$O was added whereby the product crystallized to yield 0.25 g (10%); mp 133–135° C.; $^1$H NMR (CDCl$_3$) δ 1.39 (d,12H), 3.10 (m, 2H), 3.54 (m, 4H), 4.05 (m, 2H), 4.72 (t, 2H), 7.38 (m, 5H), 11.8 (br, 1H). Anal. (C$_{19}$H$_{27}$NO$_3$.HCl) C, H, N.

EXAMPLE 92

2-(Diisopropylamino)ethyl 1-(3-aminophenyl)cyclobutanecarboxylate Hydrochloride 2-(Diisopropylamino)ethyl 1-(3-nitrophenyl)-cyclobutanecarboxylate hydrochloride prepared in Example 49 above (0.2 g, 0.52 mmol) was dissolved in EtOH. Palladium (10%) on charcoal (25 mg) was added and the mixture was hydrogenated at atmospheric pressure for 2 h. The catalyst was then filtered off and the solvent was evaporated. The residue was dissolved in EtOAc and washed with NaOH. The aqueous layer was extracted with EtOAc. The combined organic layers were washed with H$_2$O, dried (MgSO$_4$) and concentrated to afford the free base that was dissolved in Et$_2$O and HCl (g)/Et$_2$O was added dropwise. The afforded pink crystals were filtered off to give 67 mg (36%) of the hydrochloride salt, mp 78–88° C.; $^1$H NMR (CD$_3$OD) δ 1.30 (m, 12H), 1.88–2.20 (m, 2H); 2.55 (m, 2H), 2.90 (m, 2H), 3.43 (t, 2H), 3.67 (m, 2H), 4.42 (t, 2H), 7.27–7.55 (m, 4H). Anal. (C$_{19}$H$_{30}$N$_2$O$_2$.1HCl) C; H: calcd, 8.2; found, 8.9; N: calcd, 7.2; found, 6.7.

EXAMPLE 93

2-(Diisopropylamino)ethyl 1-phenyl-3-cis-hydroxycyclobutanecarboxylate Hydrochloride NaBH$_4$ (16 mmol) was added to a solution of 2-(diisopropylamino)ethyl 1-phenyl-3-oxocyclobutanecarboxylic acid (1.94 mmol), prepared in Example 91 above, kept at −60° C. The reaction mixture was allowed to warm to room temperature and quenched with 6 M HCl (4 mL). The solvent was evaporated and the remaining oil partitioned between 2 M NaOH and Et$_2$O. The crude isomer mixture was chromatographed on silica using CHCl$_3$—MeOH-conc. ammonia 98:2:0.2 as eluent. The pure cis isomer fractions were pooled and the solvent was evaporated. The residue was dissolved in Et$_2$O and HCl (g)/Et$_2$O was added whereby the product was collected as a colourless oil. The yield was 0.08 g (12%); $^1$H-NMR (CD$_3$OD) δ 1.24 (d, 12H), 2.35 (m, 2H), 3.21 (m, 2H), 3.38 (t, 2H), 3.59 (m, 2H), 4.46 (m, 3H), 7.29 (m, 5H). Anal. (C$_{19}$H$_{30}$ClNO$_3$.0.5H$_2$O) C, H, N.

III. Arylcyclopentane carboxylic esters

EXAMPLE 94

Starting Material

1-(2-Thienyl)cyclopentanecarboxylic Acid

NaH (80% dispersion in mineral oil, 127 mmol) was washed several times with n-pentane and suspended in DMF. A mixture of 1-($^2$-thienyl)acetonitrile (60 mmol) and 1,4-dibromobutane (60 mmol) in DMF was added dropwise. The reaction mixture was stirred at room temperature for 3 h. Excess hydride was then decomposed by the cautious addition of H$_2$O. Extraction with toluene, drying of the organic layer (MgSO$_4$) and evaporation of the solvent afforded 1-(2-thienyl)cyclopentaneacetonitrile that was chromatographed on silica gel using petroleumether-EtOAc 97:3 as eluent; $^1$H NMR (CDCl$_3$) δ 1.94 (m, 4H), 2.12 (m, 2H), 2.50 (m, 2H), 6.96 (dd, 1H), 7.10 (dd, 1H), 7.23 (dd, 1H). The acetonitrile was then refluxed with 15 M KOH (30 mL) in ethyleneglycol (70 mL) for 2 h. It was then allowed to cool to room temperature, ether and H$_2$O were added and the layers were separated. The aqueous layer was acidified and extracted with ether. The organic layer was dried (MgSO$_4$) and concentrated to provide the desired carboxylic acid with a yield of 5.8 g (49%).

EXAMPLE 95

Starting Material

1-(3-Thienyl)cyclopentanecarboxylic Acid

The title compound was produced in an analogous manner to that in Example 94 from 1-(3-thienyl)acetonitrile and 1,4-dibromobutane; $^1$H NMR (CDCl$_3$) δ 1.99 (m, 6H), 2.45 (m, 2H), 7.11 (dd, 1H), 7.29 (dd, 1H), 7.36 (dd, 1H). The yield of the desired carboxylic acid was 10.5 g (49%).

EXAMPLE 96

Starting Material

1Phenyl-3,3-dimethylcyclopentanecarboxylic Acid

The title compound was produced in an analogous manner to that in Example 94 from 1-phenylacetonitrile and de-O-p-toluene-sulfonyl-2-dimethyl-1,4-butanediol. The obtained 1-phenyl-3-dimethylcyclopentaneacetonitrile was chromatographed on silica using petroleumether-EtOAc 97:3 as eluent; $^1$H NMR (CDCl$_3$) δ 1.13 (s, 3H), 1.30 (s, 3H), 1.77 (m, 1H), 1.98 (m, 2H), 2.24 (m, 1H), 2.40 (m, 1H), 2.51 (m, 1H), 7.43 (m, 5H). The yield of the desired carboxylic acid was 1.8 g (42%).

EXAMPLE 97

2-(Diethylamino)ethyl 1-(2-thienyl) cyclopentanecarboxylate Hydrochloride 1-(2-thienyl)cyclopentanecarboxylic acid (3.1 mmol), prepared in Example 94 above, was refluxed with SOCl$_2$ (0.6 mL) in 4 mL toluene. After 4 h, the reaction mixture was evaporated and the residue was dissolved in toluene. 2-Diethylaminoethanol (9.3 mmol) was added and the mixture was stirred at room temperature overnight. The crude was chromatographed on silica gel using toluene-Et$_3$N 95:5 as eluent. The yield was 0.79 g (76%); mp 122–123° C.; $^1$H NMR (CDCl$_3$) δ 1.28 (t, 6H), 1.75 (m, 4H), 2.13 (m, 2H), 2.50 (m, 2H), 2.92 (m, 4H), 3.22 (m, 2H), 4.60 (t, 2H), 6.95 (dd, 2H), 7.19 (dd, 1H), 12.4 (br, 1H). Anal. (C$_{16}$H$_{25}$NO$_2$S.HCl) C, H, N.

EXAMPLE 98

2-(Diethylamino)ethyl 1-(3-thienyl) cyclopentanecarboxylate Hydrochloride

The title compound was produced in an analogous manner to that in Example 97 from 1-(3-thienyl) cyclopentanecarboxylic acid, prepared in Example 95, and 2-diethylaminoethanol. The crude was chromatographed on silica gel using toluene-Et$_3$N 97:3 as eluent. The yield was 0.74 g (53%); mp 121–122° C.; $^1$H NMFW (CDCl$_3$) δ 1.25 (t, 6H), 1.72 (m, 4H), 2.01 (m, 2H), 2.45 (m, 2H), 2.87 (m, 4H), 3.19 (t, 2H), 4.57 (t, 2H), 7.03 (dd, 1H), 7.13 (dd, 1H), 7.30 (dd, 1H), 12.3 (br, 1H). Anal. (C$_{16}$H$_{25}$NO$_2$S.HCl) C, H, N.

EXAMPLE 99

2-(Diisopropylamino)ethyl 1-phenylcyclopentanecarboxylate Hydrochloride

The title compound was produced in an analogous manner to that in Example 97 by reacting 1-phenylcyclopentanecarbonyl chloride with 2-diisopropylaminoethanol at 80° C. for 8 h. The reaction mixture was filtered and chromatographed on silica gel using toluene-Et$_3$N 95:5 as eluent. The yield was 1.5 g (78%); mp 124–128° C.; $^1$H NMR (D$_2$O) δ 1.31 (d, 12H), 1.79 (m, 4H), 2.12 (m, 2H), 2.58 (m, 2H), 3.45 (t, 2H), 3.67 (m, 2H), 4.43 (t, 2H), 7.4 (m, 1H), 7.48–7.54 (m, 4H). Anal. (C$_{20}$H$_{31}$NO$_2$.HCl) C, H, N.

EXAMPLE 100

2-(Diisopropylamino)ethyl 1-(2-thienyl) cyclopentanecarboxylate Hydrochloride

The title compound was produced in an analogous manner to that in Example 97 from 1-(2-thienyl) cyclopentanecarboxylic acid, prepared in Example 94, and 2-diisopropylaminoethanol. The crude was chromatographed on silica gel using toluene-Et$_3$N 98:2 as eluent. The yield was 0.6 g (54%); mp 147–148° C.; $^1$H NMR (CDCl$_3$) δ 1.42 (m, 12H), 1.76 (m, 4H), 2.11 (m, 2H), 2.52 (m, 2H), 3.09 (m, 2H), 3.57 (m, 2H), 4.71 (t, 2H), 6.94 (m, 2H), 7.20 (dd, 1H), 11.7 (br, 1H). Anal. (C$_{18}$H$_{29}$NO$_2$S.HCl) C, H, N.

EXAMPLE 101

2-(Diisopropylamino)ethyl 1-(3-thienyl) cyclopentanecarboxylate

The title compound was produced in an analogous manner to that in Example 97 from 1-(3-thienyl) cyclopentanecarboxylic acid, prepared in Example 95, and 2-diisopropylaminoethanol. The crude was chromatographed on silica gel using toluene-Et$_3$N 97:3 as eluent. The yield was 0.99 g (66%); mp 126–127° C.; $^1$H NMR (CDCl$_3$) δ 1.39 (m, 12H), 1,71 (m, 4H), 2.00 (m, 2H), 2.49 (m, 2H), 3.06 (m, 2H), 3.55 (m, 2H), 4.68 (t, 2H), 7.03 (dd, 1H), 7.12 (dd, 1H), 7.28 (dd, 1H) 11.7 (br, 1H). Anal. (C$_{18}$H$_{29}$NO$_2$S.HCl) C, H. N.

EXAMPLE 102

(1-Methyl-3-piperidino)methyl 1-(2-thienyl) cyclopentanecarboxylate Hydrochloride The title compound was produced in an analogous manner to that in Example 97 from 1-(2-thienyl) cyclopentanecarboxylic acid, prepared in Example 94, and (1-methyl-3-piperidino)methanol. The crude was chromatographed on silica gel using toluene-Et$_3$N 95:5 as eluent. The yield was 0.94 g (88%); mp 134–135° C.; $^1$H NMR (CDCl$_3$) δ 1.04 (m, 1H), 1.74 (m, 6H), 2.03–2.65 (m, 11H), 3.12 (d, 1H), 3.40 (d, 1H), 4.03 (m, 2H), 6.98 (dd, 2H), 7.21 (dd, 1H), 12.3 (br, 1H). Anal. (C$_{17}$H$_{25}$NO$_2$S.HCl) C, H, N.

EXAMPLE 103

(1-Methyl-3-piperidino)methyl 1-(3-thienyl) cyclopentanecarboxylate Hydrochloride The title compound was produced in an analogous manner to that in Example 97 from 1-($^3$-thienyl) cyclopentanecarboxylic acid, prepared in Example 95, and (1-methyl-3-piperidino)methanol. The crude was chromatographed on silica gel using toluene-Et$_3$N 97:3 as eluent. The yield was 0.82 g (57%); mp 156–157° C.; $^1$H NMR (CDCl$_3$) δ 0. 99 (m, 1H), 1.65–3.65 (m, 17H), 3.07 (d, 1H), 3.39 (d, 1H), 4.00 (m, 2H), 7.08 (dd, 1H), 7.16 (dd, 1H), 7.29 (dd, 1H), 12.4 (br, 1H). Anal. (C$_{17}$H$_{25}$NO$_2$S.HCl) C, H, N.

EXAMPLE 104

1-Methyl-4-piperidinyl 1-(2-thienyl) cyclopentanecarboxylate Hydrochloride

The title compound was produced in an analogous manner to that in Example 97 from 1-(2-thienyl) cyclopentanecarboxylic acid, prepared in Example 94, and 1-methyl-4-hydroxypiperidine. The crude was chromatographed on silica gel using toluene-Et$_3$N 96:4 as eluent. The yield was 0.97 g (47%); mp 164–165° C.; $^1$H NMR (CDCl$_3$) δ 1.77, (s, 4H), 1.93 (m, 2H), 2.13 (m, 2H), 2.49 (m, 6H), 2.62 (s, 3H), 3.20 (m, 2H), 5.01 (s, 1H), 6.97 (m, 2H), 7.22 (d, 1H). Anal. (C$_{16}$H$_{23}$NO$_2$S.HCl) C, H, N.

EXAMPLE 105

1-Methyl-4-piperidinyl 1-(3-thienyl) cyclopentanecarboxylate Hydrochloride

The title compound was produced in an analogous manner to that in Example 97 from 1-(3-thienyl)

cyclopentanecarboxylic acid, prepared in Example 95, and 1-methyl-4-hydroxypiperidine. The crude was chromatographed on silica using toluene-Et$_3$N 96:4 as eluent. The yield was 0.88 g (32%); mp 163–164° C.; $^1$H NMR (CDCl$_3$) δ 1.74–2.62 (m, 17H), 3.14 (s, 2H), 4.98 (s, 1H), 7.05 (dd, 1H), 7.15 (d, 1H), 7.30 (d, 1H), 12.3 (br, 1H). Anal. (C$_{16}$H$_{23}$NO$_2$S.HCl) C, H. N.

EXAMPLE 106

3-Quinuclidinyl 1-phenylcyclopentanecarboxylate Hydrochloride

The title compound was produced in an analogous manner to that in Example 97 by reacting 1-phenylcyclopentane carbonyl chloride with 3-quinuclidinol at 80° C. for 22 h. The reaction mixture was filtered and chromatographed on silica gel using toluene-Et$_3$N 95:5 as eluent. The yield was 0.7 g (41%); mp 201–203° C.; $^1$H NMR (D$_2$O) δ 1.79 (m, 6H), 1.92 (m, 1H), 2.07 (m, 3H), 2.34 (m, 1H), 2.66 (m, 2H), 3.04 (q, !H), 3.13 (d, 1H), 3.25–3.37 (m, 3H), 3.67 (m, 1H), 5.13 (m, 1H), 7.41 (t, 1H), 7.48 (t, 2H), 7.53 (d, 2H). Anal. (C$_{19}$H$_{25}$NO$_2$.HCl) C, H, N.

EXAMPLE 107

3-Quinuclidinyl 1-(2-thienyl) cyclopentanecarboxylate Hydrochloride

The title compound was produced in an analogous manner to that in Example 97 from 1-(2-thienyl) cyclopentanecarboxylic acid, prepared in Example 94, and 3-quinuclidinol. The crude was chromatographed on silica gel using toluene-Et$_3$N 96:4 as eluent. The yield was 0.2 g (13%); mp 209–211° C.; $^1$H NMR (CDCl$_3$) δ 1.55–2.26 (m, 10H), 2.38 (m, 1H), 2.46 (m, 2H), 3.02 (m, 2H), 3.27 (m, 3H), 3.50 (m, 1H), 5.02 (m, 1H), 6.94 (dd, 2H), 7.21 (dd, 1H). Anal. (C$_{17}$H$_{23}$NO$_2$S.HCl) C, H, N.

EXAMPLE 108

3-Quinuclidinyl 1-(3-thienyl) cyclopentanecarboxylate Hydrochloride

The title compound was produced in an analogous manner to that in Example 97 from 1-(3-thienyl) cyclopentanecarboxylic acid, prepared in Example 95, and 3-quinuclidinol. The arylcyclopentanecarbonylchloride was refluxed with 3-quinuclidinol for three days. The crude was chromatographed on silica gel using toluene-Et$_3$N 89:11 as eluent. The yield was 1.73 g (40%); mp 213–215° C.; $^1$H NMR (CDCl$_3$) δ 1.61–2.11 (m, 10H), 2.32 (m, 1H), 2.49 (m, 2H), 2.99 (m, 2H), 3.27 (m, 3H), 3.58 (m, 1H), 5.00 (m, 1H), 7.02 (dd, 1H), 7.13 (dd, 1H), 7.28 (dd, 1H), 12.3 (br, 1H). Anal. (C$_{17}$H$_{23}$NO$_2$S.HCl) C, H, N.

EXAMPLE 109

3-Endo-(1-azabicyclo[3.3.1]nonyl 1-phenylcyclopentanecarboxylate Hydrochloride

The title compound was produced in an analogous manner to that in Example 97 by reacting 1-phenylcyclopentanecarbonyl chloride with 3-hydroxy-1-azabicyclo[3.3.1]nonane at 80° C. for 18 h. The reaction mixture was filtered and chromatographed on silica gel using toluene-Et$_3$N 95:5 as eluent in order to separate the two afforded isomers. The endo isomer eluted earlier than the exo isomer. The yield of the endo isomer was 90 mg (7%); mp 242–246° C.; $^1$H NMR (D$_2$O) δ 1.68–1.88 (m, 7H), 1.88–2.08 (m, 4H), 2.14 (m, 1H), 2.36 (s, 1H), 2.55 (m, 2H), 3.25 (m, 3H), 3.42 (m, 2H), 3.55 (m, 1H), 5.55 (m, 1H), 7.39 (m, 1H), 7.47 (m, 4H) Anal. (C$_{20}$H$_{27}$NO$_2$.HCl) C, H, N.

EXAMPLE 110

3-Exo-(1-azabicyclo[3.3.1]nonyl] 1-phenylcyclopentanecarboxylate Hydrochloride

The yield of the exo isomer afforded in the synthesis in Example 109 above was 200 mg (16%); mp 195–198° C.; $^1$H NMR (D$_2$O) δ 1.42 (m, 2H), 1.68–1.85 (m, 6H), 2.02–2.16 (m, 3H), 2.22 (s, 1H), 2.36 (m, 1H), 2.58 (m, 2H), 3.02 (q, 1H), 3.18 (d, 1H), 3.23–3.32 (m, 3H), 3.82 (q, 1H), 5.25 (t, 1H), 7.40 (t, 1H), 7.45–7.52 (m, 4H). Anal. (C$_{20}$H$_{27}$NO$_2$.HCl) C, H, N.

EXAMPLE 111

3-Tropanyl 1-(2-thienyl)cyclopentanecarboxylate Hydrochloride

The title compound was produced in an analogous manner to that in Example 97 from 1-(2-thienyl) cyclopentanecarboxylic acid, prepared in Example 94, and 3-tropanol. The crude was chromatographed on silica using toluene-Et$_3$N 93:7 as eluent. The yield was 0.94 g (28%); mp 236–237° C.; $^1$H NMR (CDCl$_3$) δ 1.74 (m, 8H), 2.08 (m, 4H), 2.48 (m, 2H), 2.70 (s, 3H), 2.97 (d, 2H), 3.66 (m, 2H), 5.08 (m, 1H), 6.95 (dd, 2H), 7.19 (m, 1H). Anal. (C$_{18}$H$_{25}$NO$_2$S.HCl) C, H, N.

EXAMPLE 112

2-(Diisopropylamino)ethyl 1-phenyl-3,3-dimethylcyclopentanecarboxylate Hydrochloride The title compound was produced in an analogous manner to that in Example 97 from 1-phenyl-3,3-dimethylcyclopentanecarboxylic acid, prepared in Example 96, and 2-diisopropylaminoethanol. The crude was chromatographed on silica gel using toluene-Et$_3$N 98:2 as eluent. The yield was 0.83 g (52%); The hydrochloride salt was collected as a colourless oil; $^1$H NMR (CDCl$_3$) δ 1.00 (s, 3H), 1.08 (s, 3H), 1.34 (m, 12H), 1.54 (m, 2H), 1.87 (d, 1H), 2.11 (m, 1H), 2.66 (m, 2H), 2.98 (m, 2H), 3.49 (m, 2H), 4.64 (t, 2H), 7.28 (m, 5H), 11.5 (br, 1H). Anal. (C$_{22}$H$_{35}$NO$_2$.HCl) C, H, N.

IV. Arylcyclohexane carboxylic esters

EXAMPLE 113

Starting Material

1-Phenyl-4-methoxycyclohexanecarboxylic Acid

NaBH$_4$ (20 mmol) in H$_2$O (7 mL) was added to a solution of 4-cyano-4-phenylcyclohexanone (25 mmol) in THF. The reaction mixture was stirred at ambient temperature for 3 h and then quenched with HOAc. The filtered solution was evaporated and the residue was taken up in Et$_2$O/brine. The organic phase was dried (MgSO$_4$) and then evaporated. The afforded alcohol was dissolved in THF and dripped into a suspension of NaH (24.5 mmol) washed several times with hexane. After 30 min of stirring, MeI (26 mmol) was carefully added, the mixture was stirred for another 5 min and then evaporated. The residue was taken up in Et$_2$O/brine, the organic layer was dried (MgSO$_4$) and then evaporated. The remaining oil was refluxed with KOH (25%, 300 mL) in ethyleneglycol (250 mL) for 3 days. The cooled solution was washed with Et$_2$O. The aqeuous layer was acidified with conc. HCl and extracted with Et$_2$O. The organic layer was dried and evaporated affording 4.6 g (78%) of the desired product; $^1$H NMR (CDCl$_3$) δ 1.51–1.73 (m, 4H), 2.02 (m, 2H), 2.64 (m, 2H), 3.21 (m, 1H), 3.35 (s, 3H), 7.20–7.45 (m, 5H), 10.2 (br, 1H).

EXAMPLE 114

Starting Material

1-Phenyl-4-oxocyclohexanecarboxylic Acid

4-Cyano-4-phenylcyclohexanone (25 mmol) was refluxed for 2 h with p-toluenesulfonic acid (2.5 mmol) and ethyleneglycol (30 mmol) in toluene (150 mL) using a Dean-Stark trap. The reaction mixture was partitioned between Et$_2$O and 2 M NaHCO$_3$. The organic layer was dried (Na$_2$SO$_4$) and evaporated. The resulting oil was refluxed with KOH (40%, 200 mL) in ethyleneglycol (120 mL) for 3 h. Conc. HCl was added and the mixture was allowed to cool. It was than extracted with Et$_2$O, dried (Na$_2$SO$_4$) and evaporated affording 4.4 g (81%) of the desired compound; $^1$H NMR (CDCl$_3$) δ 2.2–2.5 (m, 4H), 2.55 (m, 2H), 2.74 (m, 2H), 7.25–7.50 (m, 5H), 8.0 (br, 1H).

EXAMPLE 115

Starting Material

1-Phenyl-3,3-dimethylcyclohexanecarboxylic Acid

NaH (60% dispersion in mineral oil, 72.3 mmol) was washed several times with n-hexane and suspended in DMF. A mixture of phenylacetonitrile (24.1 mmol) and de-O-p-toluene-sulfonyl-2,2-dimethyl-1,5-pentanediol (24.1 mmol) in DMF was added dropwise. The reaction mixture was stirred at 70° C. for 3 h and DMF was evaporated under reduced pressure. Excess hydride was then decomposed by the cautious addition of H$_2$O. Extraction with Et$_2$O, drying of the organic layer (MgSO$_4$) and evaporation of the solvent afforded 1-phenyl-3,3-dimethylcyclohexaneacetonitrile that was chromatographed on silica using petroleumether-EtOAc 98:2 as eluent; $^1$H NMR (CDCl$_3$) δ 0.96 (s, 3H), 1.26 (m, 1H), 1.31 (m, 3H) 1.59 (m, 2H), 1.78 (m, 2H), 1.92 (m, 2H), 2.23 (m, 1H), 7.49 (m, 5H). 7.0 mmol of the nitrile was refluxed with KOH (40%, 15 mL) in ethyleneglycol (40 mL) for two days. It was then allowed to cool to room temperature and was extracted with Et$_2$O. The aqueous layer was acidified and extracted with Et$_2$O. The organic layer was dried (MgSO$_4$) and concentrated to provide 1.5 g (27%) of the desired carboxylic acid.

EXAMPLE 116

Starting Material

1Phenyl-4,4-dimethylcyclohexanecarboxylic Acid

The title compound was produced in an analogous manner to that in Example 113. 1-Phenyl-4,4-dimethylcyclohexaneacetonitrile was refluxed with KOH in ethyleneglycol for 2 days. The yield of the desired carboxylic acid was 0.55 g (12%) $^1$H NMR (CDCl$_3$) δ 0.94 (s, 3H), 1.00 (s, 3H), 1.49 (m, 2H), 1.74 (m, 2H), 1.92 (m, 4H), 7.44 (m, 5H).

EXAMPLE 117

2-(Diisopropylamino)ethyl 1-phenylcyclohexanecarboxylate Hydrochloride

1-Phenyl-cyclohexanecarboxylic acid (1 g, 4.9 mmol) was refluxed with SOCl$_2$ (15 mL). After 0.5 h, the reaction mixture was evaporated and the residue was dissolved in toluene. 2-Diisopropylaminoethanol (1.4 g, 9.8 mmol) was added and the mixture was stirred at 80° C. for 14 h. The reaction mixture was filtered and chromatographed on silica gel using toluene-Et$_3$N 95:5 as eluent. The yield was 1.5 g (84%); mp 119–122° C.; $^1$H NMR (D$_2$O) δ 1.38 (d, 12H), 1.40 (m, 1H), 1.54 (m, 2H), 1.63–1.76 (m, 3H), 1.95 (t, 2H), 2.45 (d, 2H), 3.44 (t, 2H), 3.67 (m, 2H), 4.44 (t, 2H), 7.43 (t, 1H), 7.51 (t, 2H), 7.54 (d, 2H). Anal. (C$_{21}$H$_{33}$NO$_2$.HCl) C, H, N.

EXAMPLE 118

2-(Diisopropylamino)ethyl 1-phenyl-4-methoxycyclohexanecarboxylate Hydrochloride The title compound was produced in an analogous manner to that in Example 117 from 1-phenyl-4-methoxycyclohexanecarboxylic acid, prepared in Example 113, and 2-diisopropylaminoethanol. The reaction with SOCl$_2$ was refluxed for 2 h. The yield was 1.79 g (57%); mp 129–134 ° C.; $^1$H NMR (CD$_3$OD) δ 1.24 (d, 12H), 1.42 (m2H), 1.80 (m, 2H), 2.01 (m, 2H), 2.60 (m, 2H), 3.20–3.40 (m, 6H), 3.59 (m, 2H), 4.42 (t, 2H), 7.20–7.44 (m, 5H). Anal. (C$_{22}$H$_{35}$NO$_3$.HCl) C, H, N.

EXAMPLE 119

2-(Diisopropylamino)ethyl 1-phenyl-4-oxocyclohexanecarboxylate Hydrochloride

The title compound was produced in an analogous manner to that in Example 117 from 1-phenyl-4-oxocyclohexanecarboxylic acid, prepared in Example 114, and 2-diisopropylaminoethanol. The amine salt was recrystallized from acetone/Et$_2$O. The yield was 0.28 g (28%); mp 158–162° C.; !H NMR (CD$_3$OD) δ 1.25 (m, 12H), 1.57–2.08 (m, 4H), 2.40 (m, 3H), 2.66 (m, 1H), 3.36 (m, 2H), 3.59 (m, 2H), 4.44 (m, 2H), 7.20–7.55 (m, 5H). Anal. (C$_{21}$H$_{31}$NO$_3$.HCl) C, H, N.

EXAMPLE 120

3-Quinuclidinyl 1-phenylcyclohexanecarboxylate Hydrochloride

The title compound was produced in an analogous manner to that in Example 117 by reacting 1-phenylcyclohexanecarbonyl chloride with 3-quinuclidinol at 80° C. for 25 h. The reaction mixture was filtered and chromatographed on silica gel using toluene-Et$_3$N 95:5 as eluent. The yield was 0.55 g (31%); mp 215–220° C.; $^1$H NMR (D$_2$O) δ 1.38 (m, 1H), 1.53 (q, 2H), 1.62–1.82 (m, 5H), 1.94 (m, 3H), 2.07 (m, 1H), 2.34 (s, 1H), 2.48 (m, 2H), 3.03 (q, 1H), 3.15 (d, 1H), 3.26–3.39 (m, 3H), 3.69 (q, 1H), 5.18 (m, 1H), 7.41 (t, 1H), 7.50 (t, 2H), 7.57 (d, 2H). Anal. (C$_{20}$H$_{27}$NO$_2$.HCl) C, H, N.

EXAMPLE 121

3-Quinuclidinyl 1-phenyl-4-methoxycyclohexanecarboxylate Hydrochloride

The title compound was produced in an analogous manner to that in Example 117 from 1-phenyl-4-methoxycyclohexanecarboxylic acid, prepared in Example 113, and 3-quinuclidinol. The reaction with SOCl$_2$ was refluxed for 2 h. 1-Phenyl-4-methoxycyclohexanecarbonyl chloride was reacted with the 3-quinuclidinol at 50° C. for 15 h. The yield was 0.69 g (18%); mp 189–203° C.; $^1$H NMR (CD$_3$OD) δ 1.47 (m, 2H), 1.65–2.15 (m, 8H), 2.26 (m, 1H), 2.68 (m, 2H), 2.99 (m, 2H), 3.20–3.42 (m, 7H), 3.70 (m, 1H), 5.11 (m, 1H), 7.18–7.45 (m, 5H). Anal. (C$_{21}$H$_{29}$NO$_3$.HCl) C, H, N.

EXAMPLE 122

3-Quinuclidinyl 1-phenyl-4-oxocyclohexanecarboxylate Hydrochloride

The title compound was produced in an analogous manner to that in Example 117 by reacting 1-phenyl-4-oxocyclohexanecarboxylic acid, prepared in Example 114, with 3-quinuclidinol at 50° C. for 15 h. The amine salt was recrystallized from acetone/Et$_2$O to yield was 0.11 g (2%); mp 248–251° C. d.; $^1$H NMR (CD$_3$OD) δ 1.68 (m, 3H), 1.92 (m, 3H), 2.22 (m, 1H), 2.31–2.63 (m, 5H), 2.78 (m, 1H), 2.97 (m, 2H), 3.20 (m, 3H), 3.70 (m, 1H), 5.12 (m, 1H), 7.16–7.59 (m, 5H). Anal. (C$_{20}$H$_{25}$NO$_3$.HCl) C, H, N.

EXAMPLE 123

2-(Isopropylamino)ethyl 1-phenylcyclohexanecarboxylate Hydrochloride

The title compound was produced in an analogous manner to that in Example 117 by reacting 1-phenylcyclohexanecarbonyl chloride (2.45 mmol) with BOC-protected isopropylaminoethanol (2.69 mmol) and pyridine (2.69 mmol) at room temperature overnight. The solvent was then evaporated and the residue was dissolved in EtOAc. 3 M HCl was added and the reaction mixture was stirred overnight. The mixture was then treated with NaOH and extracted with Et$_2$O and EtOAc. The combined organic layers were dried (MgSO$_4$) and concentrated in vacuo. Chromatography on silica gel using hexane-Et$_3$N 90:10 as eluent afforded 0.1 g of the free base that was dissolved in Et$_2$O and HCl (g)/Et$_2$O was added dropwise to give 0.09 g (11%) of the hydrochloride salt after filtration; mp 187–190° C.; $^1$H NMR (CD$_3$OD) δ 1.20 (d, 6H), 1.26–1.85 (m, 8H), 2.47–2.52 (m, 2H), 3.06–3.16 (m, 1H), 3.22 (t, 2H), 4.30 (t, 2H), 7.21–7.44 (m, 5H). Anal. (C$_{18}$H$_{27}$NO$_2$.HCl) C, H, N.

EXAMPLE 124

2-(Diisopropylamino)ethyl 1-phenyl-4,4-dimethylcyclohexanecarboxylate Hydrochloride The title compound was produced in an analogous manner to that in Example 117 from 1-phenyl-4,4-dimethylcyclohexanecarboxylic acid, prepared in Example 116, and 2-diisopropylaminoethanol. The crude was chromatographed on silica gel using toluene-Et$_3$N 99:1. The residue was dissolved in petroleumether and HCl/ether diluted with petroleumether was added whereby the product crystallized to yield 0.29 g (39%); mp 128–129° C.; $^1$H NMR (CDCl$_3$) δ 0.89 (s, 3H), 0.94 (s, 3H), 1.34 (m, 16H) 1.89 (m, 2H), 2.38 (m, 2H), 2.99 (m, 2H), 3.49 (m, 2H), 4.68 (t, 2H), 7.22–7.42 (m, 5H), 11.6 (br, 1H). Anal. (C$_{23}$H$_{37}$NO$_2$.HCl) C, H, N.

EXAMPLE 125

2-(Diisopropylamino)ethyl 1-phenyl-3,3-dimethylcyclohexanecarboxylate Hydrochloride The title compound was produced in an analogous manner to that in Example 117 from 1-phenyl-3,3-dimethylcyclohexanecarboxylic acid, prepared in Example 115, and 2-diisopropylaminoethanol. The crude was chromatographed on silica gel using toluene-Et$_3$N 98:2 as eluent. The residue was dissolved in petroleumether and HCl (g)/Et$_2$O diluted with petroleumether was added whereby the product crystallized to yield 0.82 g (44%); mp 167–169° C.; $^1$H NMR (CDCl$_3$) δ 0.86 (s, 3H), 0.92 (s, 3H), 1.30 (m, 15H), 1.72 (m, 3H), 2.41 (d, 1H), 2.58 (m, 1H), 3.00 (m, 2H), 3.48 (m, 2H); 4.62 (m, 2H), 7.34 (m, 5H), 11.6 (br, 1H). Anal. (C$_{23}$H$_{37}$NO$_2$.HCl) C, H, N.

EXAMPLE 126

2-(Diisopropylamino)ethyl 1-phenyl-4,4-ethylenedioxycyclohexanecarboxylate Hydrochloride 2-(Diisopropylamino)ethyl 1-phenyl-4-oxocyclohexanecarboxylate hydrochloride (3 mmol), prepared in Example 119, was refluxed for 4 h with p-toluenesulfonic acid (1.5 mmol) and ethyleneglycol (4 mmol) in toluene (50 mL) using a Dean-Stark trap. The reaction mixture was partitioned between Et$_2$O and 2 M NaHCO$_3$. The organic layer was dried (Na$_2$SO$_4$) and evaporated. The residue was dissolved in Et$_2$O and HCl (g)/Et$_2$O was added. The amine salt was recrystallized from acetone/Et$_2$O to yield 0.53 g (43%); mp 121–128° C.; $^1$H NMR (CD$_3$OD) δ 1.25 (d, 12H), 1.72 (m, 4H), 2.13 (m, 2H), 2.47 (m, 2H), 3.35 (t, 2H), 3.59 (m, 2H), 3.93 (m, 4H), 4.42 (t, 2H), 7.26–7.47 (m, 5H).

PREPARATION OF PHARMACEUTICAL COMPOSITIONS

| EXAMPLE A: Tablets of 5 mg Model batch for 1000 tablets | |
|---|---|
| I Active Compound, mesh* 70 | 5 g |
| Lactosum, Ph. Nord | 210 g |
| Amylum maidis, Ph. Nord | 75 g |
| II Kollidon 25 B.A.S.F. | 3.5 g |
| Aqua purificata | q.s. |
| III Talcum, Ph. Nord | 15 g |
| Magnesii stearas, Ph. Nord. | 1.5 g |
| Weight of 1000 tablets | 325 g |
| Weight of 1 tablet: | 325 mg |

*The mesh standard is according to the international system of code DIN 4189/1968.

Punch: 10.5 mm round, flat scored, bevel-edged.

Mix the screened substances I thoroughly and then moisten with II, whereupon the mixture is granulated through a stainless sieve No. 10 (mesh 25). Dry the granulate in an oven at a maximum temperature of 40° C., then repeat sieving through sieve No. 10. Add the substances under III and mix thoroughly. Punch tablets with a gross weight of about 325 mg.

| EXAMPLE B: Suspension for injection 5 mg/ml | |
|---|---|
| Active compound, mesh 100 | 5 mg |
| Sodium Chloride | 8 mg |
| Carboxy methylcellulose | 1 mg |
| Benzyl alcohol | 1 mg |
| Distilled water to make | 1 ml |
| EXAMPLE C: Oral Suspension 1 mg/ml | |
| Active compound, mesh 100 | 1 mg |
| Sorbitol | 600 mg |
| Flavouring compound | q.s. |

-continued

| | |
|---|---|
| Colour | q.s. |
| Water to make | 1 ml |

EXAMPLE D: Suppositoria of 5 mg

| | |
|---|---|
| Active compound | 5 mg |
| Cocoa butter | q.s. |

EXAMPLE E: Ointment 1%

| | |
|---|---|
| Active compound | 1 g |
| Triethanolamine | 1 g |
| Glycerol | 7 g |
| Cetanol | 2.5 g |
| Lanolin | 2.5 g |
| Stearic acid | 20 g |
| Sorbitan monooleate | 0.5 g |
| Sodium hydroxide | 0.2 g |
| Methyl paraben | 0.3 g |
| Propyl paraben | 0.1 g |
| Ethanol | 0.9 g |
| Water to make | 100 g |

EXAMPLE F: Capsules of 2 mg

| | |
|---|---|
| Active compound | 2 mg |
| Magnesium stearate | 2 mg |
| Talcum | 188 mg |

The substances are mixed and filled in capsules.

EXAMPLE G: 5 mg sterile powder to be dissolved in water for injection

| | |
|---|---|
| Water-soluble Active Compound | 2 mg |
| Sodium Chloride | 2 mg |
| Methyl paraben | 0.7 mg |
| Propyl paraben | 0.3 mg |

The substances are dissolved in distilled water. The solution is dispensed in vials and freeze-dried.

EXAMPLE H: Injectable solution 5 mg/ml

| | |
|---|---|
| Water-soluble Active Compound | 5 mg |
| Ascorbic acid | 1 mg |
| Sodium bisulfite | 1 mg |
| Sodium chloride | 6 mg |
| Methyl paraben | 0.7 mg |
| Propyl paraben | 0.3 mg |
| Distilled water to make | 1 ml |

In the foregoing Examples A–H relating to compositions, the Active Compounds are those covered by the general Formulae I and IA above or their addition salts with pharmaceutically acceptable inorganic or organic acids. Water-soluble Active Compounds are such addition salts or salts with a pharmaceutically acceptable inorganic or organic cation. Also, it is to be noted that two or more Active Compounds of the invention may be used in combination in the composition illustrated, and also, if desired, in combination with other pharmacologically active agents.

BIOLOGICAL EVALUATION

The pharmacological activity of compounds prepared in the Examples was tested using different in vitro methods.

Receptor binding assay

The tissue preparations and the general methods used have been described in detail elsewhere for the parotid gland[1], heart[3] and cerebral cortex[3], respectively. Male guinea pigs (250–400 g body weight) were killed by a blow on the neck and exsanguinated. The brain was placed on ice for dissection of the cerebral cortex (grey matter only). Hearts and parotid glands were dissected in a Krebs-Henseleit buffer (pH 7.4) containing 1 mM phenyl methyl sulfonyl fluoride (PMSF, a protease inhibitor). Dissected tissues were homogenised in an ice-cold sodium-potassium phosphate buffer (50 mM, pH 7.4) containing 1 mM PMSF, using a Polytron PT-10 instrument (heart, parotid) and a Potter-Elvehjem Teflon homogeniser (cortex). All homogenates were finally diluted with the ice-cold phosphate/PMSF buffer to a final protein concentration of $\leq 0.3$ mg/ml and immediately used in the receptor binding assays. Protein was determined by the method of Lowry et al. (1951)[4], using bovine serum albumin as the standard.

The muscarinic receptor affinities of unlabelled compounds of the Examples were derived from competition experiments in which the ability to inhibit the receptor specific binding of $(-)^3$H-QNB (1-quinuclidinyl[phenyl-4-$^3$])benzilate, 32–52 Ci/mmole) was monitored as previously described[3,5]. Each sample contained 10 $\mu$l of $(-)^3$H-QNB (final concentration 2 nM), 10 $\mu$l solution of test compound and 1.0 ml tissue homogenate placed in 24-well cell culture plate. Triplicate samples were incubated under conditions of equilibrium, i.e., at 25° C. for 100 minutes (heart and cerebral cortex) or 240 minutes (parotid gland), respectively. Non-specific binding was determined in the presence of 10 $\mu$M unlabelled atropine. Incubations were terminated by filtration using filtermate-196 and GF/B-Unifilters, and the radioactivity was determined by filtration liquid scintillation spectrometry.

$IC_{50}$-values (concentration of unlabelled compound producing 50% inhibition of the receptor specific $(-)^3$H-QNB binding) were graphically determined from the experimental concentration-inhibition curves. Affinities, expressed as the dissociation constants $K_i$, were calculated by correcting the $IC_{50}$ for the radioligand-induced parallel shift and differences in receptor concentration, using the method of Jacobs et al. (1975)[6]. The binding parameters for $(-)^3$H-QNB ($K_D$ and receptor densities) used in these calculations were determined in separate series of experiments[1–3].

The method has been changed from centrifugation assay to filtration assay. In order to validate the filtration assays, the $K_i$-values for atropine, AF-DX 116, 4-DAMP and pirenzepine were compared with those previously determined using centrifugation assays. The $K_i$-values of these two methods were almost identical (within the experimental error). The time of incubation was prolonged by 20–40 minutes due to the slower process of gaining 25° C. in the present samples.

Functional in vitro studies

Male guinea pigs, weighing about 300 g, were killed by a blow on the neck and exsanguinated. Smooth muscle strips of the urinary bladder were dissected in a Krebs-Henseleit solution (pH 7.4). The strip preparations were vertically mounted between two hooks in thermostatically controlled (37° C.) organ baths (5 ml). One of the hooks was adjustable and connected to a force transducer (FT 03, Grass Instruments). The Krebs-Henseleit solution was continuously bubbled with carbogen gas (93.5% $O_2$/6.5% $CO_2$) to maintain the pH at 7.4. Isometric tension was recorded by a Grass Polygraph (Model 79D). A resting tension of approximately 5 mN was initially applied on each muscle strip and the preparations were allowed to stabilise for at least 45 min. The resting tension was repeatedly adjusted and the preparations were washed several times during the stabilisation period.

Carbachol (carbamylcholine chloride) was used as the standard muscarinic receptor agonist. In each experiment, the viability of the preparations and the reproducibility of their contractile responses were initially tested by two consecutive additions of a submaximal concentration ($3 \times 10^{-6}$ M) of carbachol. A concentration-response curve to carbachol was then generated by cumulative addition of carbachol to the organ-bath (i.e., stepwise increase of the agonist concentration until the maximal contractile response was reached), followed by washing out and a resting period of at least 15 min. before a fix concentration of the test compound (antagonist) was added to the organ-bath. After 60 min. of incubation with the antagonist, a second cumulative concentration-response curve to carbachol was generated. Responses were expressed as percent of the maximal response to carbachol. $EC_{50}$-values for carbachol in the absence (control) and presence of antagonist were graphically derived and dose ratios (r) were calculated. Dissociation constants, $K_B$, for the antagonists were calculated using equation $(1)^7$, where [A] is the concentration of test compound.

$$K_B=[A]/r-1 \qquad (1)$$

The $K_i$ values obtained in the receptor binding assay for heart ($M_2$ receptor), parotid ($M_3$ receptor) and cortex ($M_1$ receptor), respectively, as well as the $K_B$ values obtained in the functional in vitro studies are presented in Tables 1 to 4 below.

A corresponding functional in vitro study to that described above was performed on a preparation of guinea pig small intestinal muscle instead of urinary bladder smooth muscle.

The $K_B$ values obtained are presented in Table 5 below.

TABLE 1

Arylcyclopropane carboxylic esters

| Compound of Example No. | $K_B$ (nM) | $K_i M_1$ (nM) | $K_i M_2$ (nm) | $K_i M_3$ (nm) |
|---|---|---|---|---|
| 4 | 18 | 5.7 | 160 | 99 |
| 5 | 260 | 10 | 50 | 160 |
| 6 | 7.0 | 5.7 | 35 | 21 |
| 7 | 26 | 4.3 | 16 | 41 |
| 8 | 390 | 69 | 520 | 1200 |
| Atropine (comparison) | 0.7 | 0.3 | 0.9 | 0.9 |
| Oxybutynin (comparison) | 4.4 | 0.41 | 2.8 | 0.62 |

TABLE 2

Arylcyclobutane carboxylic esters

| Ex. No. | $R_3/R'3$ | Ar | $R_1$ | $R_2$ | $R_4$ | $R_5$ | $R_6$ | $R_7$ | $K_b$ | $M_1$ | $M_2$ | $M_3$ |
|---|---|---|---|---|---|---|---|---|---|---|---|---|
| 36 | diethylaminoethyl | phenyl | H | H | H | H | H | H | 14 | 4.2 | 30 | 30 |
| 37 | diethylaminopropyl | " | H | H | H | H | H | H | 37 | 7.0 | 67 | 28 |
| 38 | diethylaminoethyl | " | H | H | H | H | Me | Me | 3.4 | 0.4 | 3.9 | 1.5 |
| 39 | " | " | H | H | H | H | Et | Et | 1.8 | 27 | | |
| 40 | diisopropylaminoethyl | " | H | H | H | H | H | H | 22 | 5.8 | 15 | 66 |
| 41 | " | " | H | H | Me | H | H | H | 29 | 25 | 68 | 210 |
| 42 | " | " | H | H | H | Me | H | H | 27 | 18 | 28 | 130 |
| 43 | " | " | H | H | H | H | Me | H | 2.7 | 1.8 | 5.1 | 8.2 |
| 44 | " | " | H | H | H | H | H | Me | 1.7 | 1.4 | 6.4 | 8.1 |
| 45 | " | " | H | H | H | H | Me | Me | 1.6 | 0.3 | 2.2 | 1.6 |
| 46 | " | " | H | H | H | H | Et | Et | 19 | 1.7 | 9.2 | 14 |
| 47 | " | " | H | H | H | H | cyclobutyl | | 3.8 | 0.3 | 2.6 | 2.0 |
| 91 | " | " | H | H | H | H | oxo | | 124 | | | |
| 48 | " | " | H | H | H | H | methylene | | 3.4 | 1.2 | 3.4 | 6.3 |
| 93 | " | " | H | H | H | H | OH | H | | 74 | 160 | >500 |
| 49 | " | " | 3-nitro | H | H | H | H | H | 610 | | | |
| 50 | " | " | 4-nitro | H | H | H | H | H | 340 | 32 | 83 | 374 |
| 51 | " | " | 1-nitro | 4-nitro | H | H | H | H | 130 | 350 | 330 | 1100 |
| 92 | " | " | 3-amino | H | H | H | H | H | 35 | 22 | 94 | 180 |
| 52 | " | " | 3,4-methylenedioxy | | H | H | H | H | 40 | 13 | 5.2 | 54 |
| 53 | " | " | 2,3-benzo | | H | H | H | H | 22 | 20 | 25 | 100 |
| 54 | " | " | 3,4-benzo | | H | H | H | H | >500 | | | |
| 55 | " | 3-thienyl | H | H | H | H | H | H | 28 | 3.3 | 9.4 | 35 |
| 56 | 1-pyrrolidinoethyl | phenyl | H | H | H | H | H | H | 130 | 14 | 89 | 53 |

TABLE 2

| Ex. No. | $R_3/R'3$ | Ar | $R_1$ | $R_2$ | $R_4$ | $R_5$ | $R_6$ | $R_7$ | $K_b$ | $M_1$ | $M_2$ | $M_3$ |
|---|---|---|---|---|---|---|---|---|---|---|---|---|
| 57 | 1-methyl-2-piperidinomethyl | phenyl | H | H | H | H | H | H | 14 | 4.2 | 30 | 30 |
| 58 | 1-methyl-3-piperidinomethyl | " | H | H | H | H | H | H | 11 | 6.4 | 61 | 30 |
| 59 | " | " | H | H | H | H | Me | Me | 1.9 | 0.5 | 6.3 | 2.1 |
| 60 | 1-methyl-4-piperidino | " | H | H | H | H | H | H | 1.7 | 0.5 | 3.3 | 2.2 |
| 61 | " | " | H | H | H | H | Me | Me | 0.2 | 0.09 | 0.8 | 0.2 |
| 62 | 1-methyl-3-pyrrolidino | " | H | H | H | H | H | H | 27 | 15 | 96 | 47 |
| 63 | 3-tropanyl | " | H | H | H | H | H | H | 2.6 | 2.1 | 26 | 5.2 |
| 64 | 3-quinuclidinyl | " | H | H | H | H | H | H | 0.3 | 0.3 | 5.1 | 1.7 |
| 65 | 3-(R)-quinuclidinyl | " | H | H | H | H | H | H | 0.2 | 0.2 | 4.7 | 0.9 |

TABLE 2-continued

| Ex. No. | R₃/R'3 | Ar | R₁ | R₂ | R₄ | R₅ | R₆ | R₇ | K_b | M₁ | M₂ | M₃ |
|---|---|---|---|---|---|---|---|---|---|---|---|---|
| 66 | 3-quinuclidinyl | " | H | H | H | H | Me | Me | 0.2 | 0.1 | 0.5 | 0.3 |
| 67 | 3-(R)-quinuclidinyl | " | H | H | H | H | Me | Me | | | | |
| 68 | 3-quinuclidinyl | " | 2-Me | H | H | H | H | H | 0.4 | 0.2 | 2.8 | 1.9 |
| 69 | " | " | 3-Me | H | H | H | H | H | 0.8 | 0.6 | 8.6 | 2.3 |
| 70 | " | " | 4-Me | H | H | H | H | H | 4.3 | 2.3 | 30 | 15 |
| 71 | " | " | 2-OMe | H | H | H | H | H | 0.7 | 0.5 | 4.9 | 3.5 |
| 72 | " | " | 3-OMe | H | H | H | H | H | 8.7 | 7.6 | 57 | 38 |
| 73 | " | " | 4-OMe | H | H | H | H | H | 24 | 14 | 181 | 98 |
| 74 | " | " | 2-F | H | H | H | H | H | 0.5 | 0.3 | 8.3 | 1.9 |
| 75 | " | " | 3-F | H | H | H | H | H | 0.6 | 0.6 | 12 | 3.9 |
| 76 | " | " | 4-F | H | H | H | H | H | 2.1 | 1.0 | 24 | 5.8 |
| 77 | " | " | 4-Cl | H | H | H | H | H | 13 | 1.6 | 26 | 8.0 |
| 78 | " | " | 2-Br | H | H | H | H | H | 4.2 | 1.8 | 14 | 16 |
| 79 | " | " | 4-Br | H | H | H | H | H | | | | |
| 80 | " | " | 3-NO₂ | H | H | H | H | H | 28 | 21 | 180 | 100 |
| 81 | " | " | 3,4-methylenedioxy | H | H | H | H | H | 20 | 8.6 | 79 | 47 |
| 82 | " | " | 2,3-benzo | H | H | H | H | H | 15 | 3.6 | 18 | 21 |
| 83 | " | " | 3,4-benzo | H | H | H | H | H | 106 | 20 | 143 | 133 |
| 84 | " | 2-thienyl | H | H | H | H | H | H | 0.4 | 0.3 | 3.9 | 2.0 |
| 85 | " | 3-thienyl | H | H | H | H | H | H | 0.4 | 0.2 | 2.8 | 0.9 |
| 86 | 2-endo-methyl-3-quinuclidinyl | " | H | H | H | H | H | H | 0.7 | 0.5 | 5.3 | 2.1 |
| 87 | 2-exo-methyl-3-quinuclidinyl | " | H | H | H | H | H | H | 0.6 | 0.3 | 5.3 | 2.6 |
| 88 | 3-endo-1-azabicyclo[3.3.1]nonane-3-yl | " | H | H | H | H | H | H | 2.5 | 1.8 | 16 | 12 |
| 89 | 3-exo-1-azabicyclo[3.3.1]nonane-3-yl | " | H | H | H | H | H | H | 1.9 | 0.9 | 14 | 4.8 |
| 90 | 3-methylidenequinuclidine | " | H | H | H | H | H | H | 15 | 1.3 | 13 | 7.3 |

TABLE 3

Arylcyclopentane carboxylic esters

| Ex. No. | R₃/R'3 | Ar | R₁ | R₂ | R₄ | R₅ | R₆ | R₇ | K_b | M₁ | M₂ | M₃ |
|---|---|---|---|---|---|---|---|---|---|---|---|---|
| 97 | diethylaminoethyl | 2-thienyl | H | H | H | H | H | H | 15 | 3.2 | 31 | 28 |
| 98 | " | 3-thienyl | H | H | H | H | H | H | 15 | 3.7 | 40 | 29 |
| 99 | diisopropylaminoethyl | phenyl | H | H | H | H | H | H | 5.7 | 3.6 | 8.5 | 21 |
| 100 | " | 2-thienyl | H | H | H | H | H | H | 15 | 2.7 | 14 | 22 |
| 101 | " | 3-thienyl | H | H | H | H | H | H | 24 | 3.0 | 8.4 | 22 |
| 102 | 1-methyl-3-piperidinomethyl | 2-thienyl | H | H | H | H | H | H | 20 | 6.2 | 34 | 29 |
| 103 | " | 3-thienyl | H | H | H | H | H | H | 30 | 7.6 | 53 | 42 |
| 104 | 1-methyl-4-piperidino | 2-thienyl | H | H | H | H | H | H | 20 | 1.1 | 4.4 | 2.6 |
| 105 | " | 3-thienyl | H | H | H | H | H | H | 2.2 | 0.7 | 5.0 | 3.8 |
| 106 | 3-quinuclidinyl | phenyl | H | H | H | H | H | H | 0.4 | 0.4 | 4.2 | 1.8 |
| 107 | " | 2-thienyl | H | H | H | H | H | H | 0.7 | 0.3 | 5.8 | 1.6 |
| 108 | " | 3-thienyl | H | H | H | H | H | H | 0.3 | 0.3 | 5.6 | 1.6 |
| 109 | 3-exo-1-azabicyclo[3.3.1]nonane-3-yl | phenyl | H | H | H | H | H | H | 2.4 | 1.0 | 16 | 4.3 |
| 110 | 3-endo-1-azabicyclo[3.3.1]nonane-3-yl | phenyl | H | H | H | H | H | H | 0.2 | 0.5 | 1.2 | 3.1 |
| 111 | 3-tropanyl | 2-thienyl | H | H | H | H | H | H | 12 | 3.3 | 21 | 10 |
| 112 | diisopropylaminoethyl | phenyl | H | H | H | H | Me | Me | −30 | | | |

TABLE 4

Arylcyclohexane carboxylic esters

| Ex. No. | R3/R'3 | Ar | R1 | R2 | R4 | R5 | R6 | R7 | R8 | R9 | $K_b$ | $M_1$ | $M_2$ | $M_3$ |
|---|---|---|---|---|---|---|---|---|---|---|---|---|---|---|
| 117 | diisopropylaminoethyl | phenyl | H | H | H | H | H | H | H | H | 21 | 3.5 | 9.2 | 29 |
| 118 | " | — | H | H | H | H | H | H | OMe | H | 29 | 39 | 55 | 441 |
| 119 | " | " | H | H | H | H | H | H | oxo | | 234 | | | |
| 126 | " | " | H | H | H | H | H | H | ethylene-dioxy | | 5 | 15 | 37 | 199 |
| 120 | 3-quinuclidinyl | " | H | H | H | H | H | H | H | H | 0.4 | 0.3 | 4.2 | 1.8 |
| 121 | " | " | H | H | H | H | H | H | OMe | H | 2.0 | 1.7 | 9 | 9.3 |
| 122 | " | " | H | H | H | H | H | H | oxo | | 16 | 3.6 | 83 | 31 |
| 123 | isopropylaminoethyl | " | H | H | H | H | H | H | H | H | | | | |
| 124 | diisopropylaminoethyl | " | H | H | H | H | Me | Me | H | H | ~50 | | | |
| 125 | " | " | H | H | H | H | H | H | Me | Me | ~400 | | | |

TABLE 5

| Compound of Example No. | $K_B$ (nM) |
|---|---|
| 99 | 3.9 |
| 117 | 0.41 |
| Darifenacin (comparison) | ~10 |

As shown in the Tables, the tested compounds exhibit high activity and specificity as antagonists for muscarinic receptor mediated bladder contraction. They also show a high affinity and specificity to intestinal muscle.

REFERENCES

1. Nilvebrant, L.; Sparf, B. Muscarinic receptor binding in the parotid gland. Different affinities of some anticholinergic drugs between the parotid gland and ileum. Scand. J. Gastroenterol. 1982, 17 (suppl. 72), 69–77.
2. Nilvebrant, L.; Sparf, B. Muscarinic receptor binding in the guinea pig urinary bladder. Acta Pharmacol. et Toxicol. 1983 a, 52, 30–38.
3. Nilvebrant, L; Sparf, B. Dicyclomine, benzhexol and oxybutynin distinguish between sub-classes of muscarinic binding-sites. Eur. J. Pharmacol. 1986, 123, 133–143.
4. D Lowry, 0. H.; Rosebrough, N. J.; Farr, A. L.; Randall, R. J. Protein measurement with the Folin phenol reagent. J. Biol. Chem. 1951, 193, 265–275.
5. Nilvebrant, L.; Sparf, B. Differences between binding affinities of some antimuscarinic drugs in the parotid gland and those in the urinary bladder and ileum. Acta Pharmacol. et Toxicol. 1983 b, 53, 304–313.
6. Jacobs, S.; Chang, K. -J.; Cuatrecasas, P. Estimation of hormone receptor affinity by competitive displacement of labelled ligand. Effects of concentration of receptor and labelled ligand. Biochem. Biophys. Res. Commun. 1975, 66, 687–692.
7. Schild, H. I. pAx and competitive drug antagonism. Br. J. Pharmacol. Chemother. 1949, 4, 277–280.

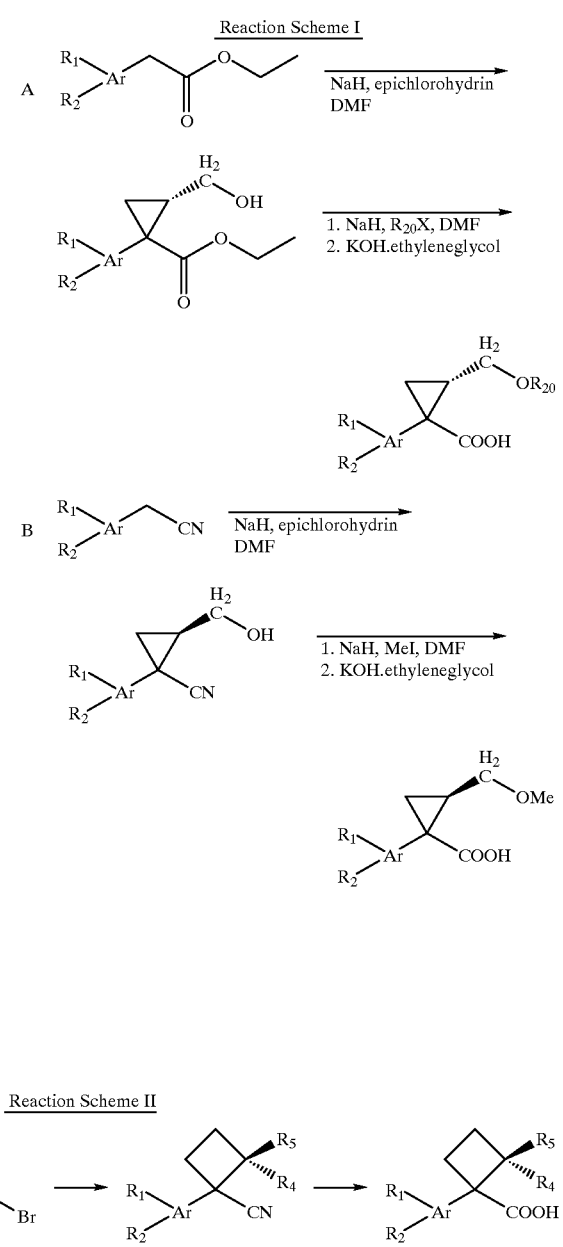

Reaction Scheme I

Reaction Scheme II

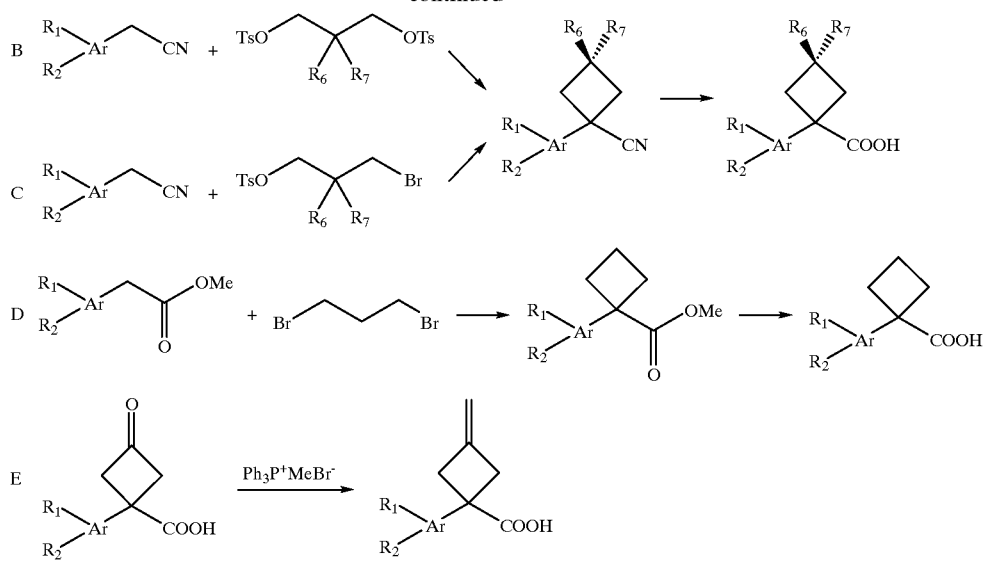
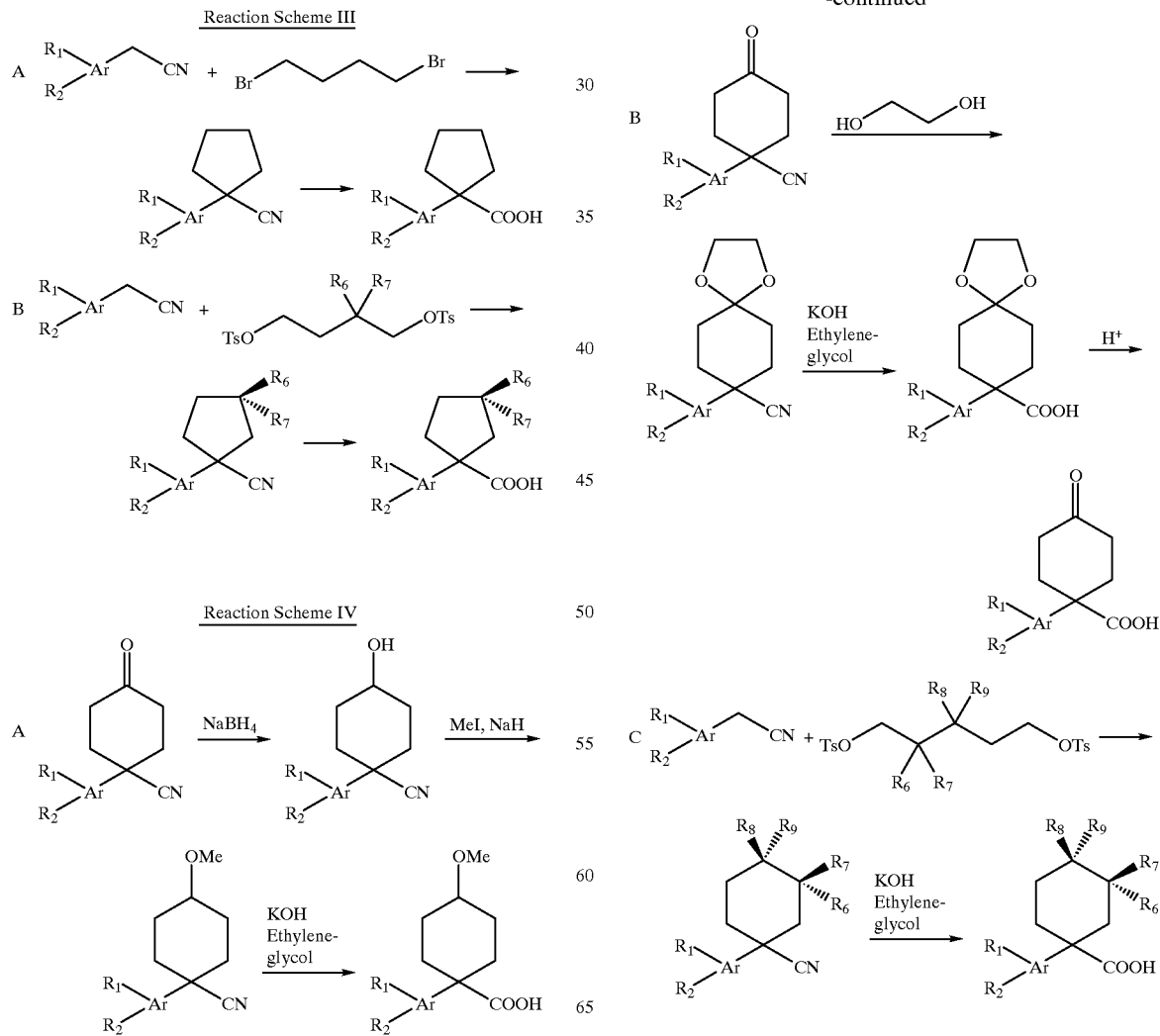

What is claimed is:

1. A method of treating a living body suffering from a disorder related to urinary incontinence or irritable bowel syndrome (IBS), which method comprises the step of administering to said living body an effective amount of a compound selected from
- 2-(diisopropylamino)ethyl 1-phenyl-cyclopentanecarboxylate; or
- 2-(diisopropylamino)ethyl 1-phenyl-cyclohexanecarboxylate, or a pharmaceutically acceptable salt thereof.

2. The method of claim 1, wherein said compound is -2-(diisopropylamino)ethyl 1-phenyl-cyclopentanecarboxylate or a pharmaceutically acceptable salt thereof.

3. The method of claim 1, wherein said compound is -2-(diisopropylamino)ethyl 1-phenyl-cyclopentanecarboxylate or a pharmaceutically acceptable salt thereof and said disorder is related to irritable bowel syndrome (IBS).

* * * * *